US012678412B2

(12) United States Patent
McGuire et al.

(10) Patent No.: US 12,678,412 B2
(45) **Date of Patent: *Jul. 14, 2026**

(54) SUBSTITUTED TOLANS FOR THE MODULATION OF MICROBIAL COLONIZATION

(71) Applicant: BioMendics, LLC, Rootstown, OH (US)

(72) Inventors: Karen M. McGuire, Rootstown, OH (US); Chun-che Tsai, Rootstown, OH (US); Emily L. Plocinik, Rootstown, OH (US); Aleesha M. McCormick, Rootstown, OH (US)

(73) Assignee: BioMendics, LLC, Rootstown, OH (US)

(*) Notice: Subject to any disclaimer, the term of this patent is extended or adjusted under 35 U.S.C. 154(b) by 482 days.

This patent is subject to a terminal disclaimer.

(21) Appl. No.: 17/833,216

(22) Filed: Jun. 6, 2022

(65) Prior Publication Data

US 2022/0296538 A1 Sep. 22, 2022

Related U.S. Application Data

(63) Continuation of application No. 16/633,979, filed as application No. PCT/US2018/043833 on Jul. 26, 2018, now Pat. No. 11,351,126.

(60) Provisional application No. 62/676,676, filed on May 25, 2018, provisional application No. 62/537,661, filed on Jul. 27, 2017.

(51) Int. Cl.

| | |
|---|---|
| ***A61K 31/01*** | (2006.01) |
| ***A61K 31/045*** | (2006.01) |
| ***A61K 31/05*** | (2006.01) |
| ***A61K 35/741*** | (2015.01) |
| ***A61P 31/04*** | (2006.01) |

(52) U.S. Cl.

CPC ............ *A61K 31/05* (2013.01); *A61K 35/741* (2013.01); *A61P 31/04* (2018.01)

(58) Field of Classification Search

CPC ...... A61K 31/01; A61K 31/045; A61K 31/05; A61K 31/09; A61K 31/085

USPC .................................................. 514/720, 733

See application file for complete search history.

(56) References Cited

U.S. PATENT DOCUMENTS

| | | | | |
|---|---|---|---|---|
| 3,840,527 | A | 10/1974 | Moore et al. | |
| 8,716,355 | B2 | 5/2014 | Tsai | |
| 11,351,126 | B2 * | 6/2022 | McGuire ................ | A61K 31/05 |
| 2002/0103262 | A1 | 8/2002 | Docherty et al. | |
| 2003/0203974 | A1 | 10/2003 | Docherty et al. | |
| 2011/0092578 | A1 | 4/2011 | Monte et al. | |
| 2011/0172174 | A1 | 7/2011 | Andersen et al. | |
| 2014/0178447 | A1 | 6/2014 | Modak et al. | |
| 2016/0296477 | A1 | 10/2016 | Tsai et al. | |

FOREIGN PATENT DOCUMENTS

| | | | |
|---|---|---|---|
| JP | 2004505998 | A | 2/2004 |
| WO | 0213764 | A2 | 2/2002 |
| WO | 2002013764 | A2 | 2/2002 |
| WO | WO2002/13764 | * | 2/2002 |
| WO | 2009126700 | A1 | 10/2009 |
| WO | 2011092578 | A1 | 8/2011 |

OTHER PUBLICATIONS

European Communication Pursuant to Article 94(3) EPC, Application No. 18838848.2, dated Jul. 3, 2024.

First Chinese Office Action, Application No. 201880055664.4, dated Oct. 9, 2022.

Korean Patent Office Notice of opinion submission, Application No. 10-2020-7005214, dated Jul. 15, 2023.

Australian Examination report, Application No. 2018306420, dated Jul. 26, 2023.

(Continued)

*Primary Examiner* — Douglas M Willis

(74) *Attorney, Agent, or Firm* — MacMillan, Sobanski & Todd, LLC

(57) ABSTRACT

Described are methods for disinfecting a physical or biological surface by contact with an antimicrobial formulation comprising a compound having the structure (I):

(I)

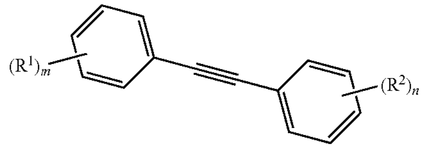

or a salt thereof, wherein each $R^1$ is independently $C_1$-$C_6$ (halo)$_p$alkyl, $C_1$-$C_6$ alkyl-RH, OH, O$C_1$-$C_6$ alkyl, or SH; each $R^2$ is independently $C_1$-$C_6$ (halo)$_p$alkyl, $C_1$-$C_6$ alkyl-RH, OH, O$C_1$-$C_6$ alkyl, or SH; each R is independently O or S; m is 1, 2, 3; n is 1, 2, or 3; and each p is independently 1, 2, or 3; provided that the compound having the structure (I) is mixed into an alcohol gel, and is not 3, 4',5-trihydroxytolan. The compounds and methods are -static and/or -cidal, depending on dose and suspected microbe. Suspected pathogenic microbes include Gram negative bacteria, such as *P. aeruginosa* and *E. coli*, Gram positive bacteria, such as *S. aureus*, including MRSA, and fungal pathogens, such as *Candida* genus and *C. albicans*. Also described are methods for inhibiting or disrupting biofilm formation of a microbe or microbes.

20 Claims, 16 Drawing Sheets
(6 of 16 Drawing Sheet(s) Filed in Color)

(56) References Cited

OTHER PUBLICATIONS

Malaysian Substantive Examination Adverse Report, Application No. PI2020000380, dated Dec. 19, 2023.

The Extended Eurpoean Search Report, Application No. 18838848.2, dated Mar. 24, 2021.

PCT International Search Report and Written Opinion, Application No. PCT/US18/43833, dated Oct. 5, 2018.

Mexico 1st Substantive Examination Requirement, Application No. MX/a/2020/001043, dated May 24, 2022.

Brazilian Office Action, Application No. BR112020001619-5, dated Jun. 22, 2022.

Japanese Office Action, Application No. JP2020527849, dated Jun. 7, 2022.

* cited by examiner

| * p<0.05 statistical significance | | | | | | |
|---|---|---|---|---|---|---|
| Treatment | A. Formulation A (High Dose) | B. Formulation A (Medium Dose) | C. Formulation A (Low Dose) | D. Vehicle | E. Tobramycin Positive control (600ug/ml) | F. Untreated Control |
| A. Formulation A (High Dose) | | 0.000* | 0.000* | 0.000* | 0.000* | 0.000* |
| B. Formulation A (Medium Dose) | 0.000* | | 0.000* | 0.000* | 0.000* | 0.000* |
| C. Formulation A (Low Dose) | 0.000* | 0.000* | | 0.000* | 0.000* | 0.001* |
| D. Vehicle | 0.000* | 0.000* | 0.000* | | 0.000* | 1.000 |
| E. Tobramycin Positive control (600ug/ml) | 0.000* | 0.000* | 0.000* | 0.000* | | 0.000* |
| F. Untreated Control | 0.000* | 0.000* | 0.000* | 1.000 | 0.000* | |

♦p<0.05 compared to All treatments

*p<0.05 compared to C. Formulation A (Low Dose), D. Vehicle, E. Tobramycin Positive control (600ug/ml) and F. Untreated Control

•p<0.05 compared to D. Vehicle, E. Tobramycin Positive control (600ug/ml) and F. Untreated Control

•p<0.05 compared to D. Vehicle and F. Untreated Control

FIG. 6B

SUBSTITUTED TOLANS FOR THE MODULATION OF MICROBIAL COLONIZATION

RELATED APPLICATIONS

This application is a continuation application of U.S. application Ser. No. 16/633,979, filed under 35 U.S.C. § 371 on Jan. 24, 2022, now U.S. Pat. No. 11,351,126; which claims priority to international application PCT/US18/43833, filed under the authority of the Patent Cooperation Treaty on Jul. 26, 2018, published; which claims priority to U.S. Provisional Application No. 62/537,661, filed under 35 U.S.C. § 111(b) on Jul. 27, 2017, as well as U.S. Provisional Application No. 62/676,676, filed under 35 U.S.C. § 111(b) on May 25, 2018. The entire disclosures of all the aforementioned applications are expressly incorporated by reference herein for all purposes.

FIELD OF THE INVENTION

The present invention relates generally to the field of microbiology and, more particularly, to compounds, formulations, and methods for the reduction of microbial growth or elimination of microbial colonies, particularly pathogens, by contacting a physical or biological surface with the compounds or a formulation of the compounds.

BACKGROUND OF THE INVENTION

The designation of a microorganism as objectionable is based upon its pathogenic potential and ability to cause infections or diseases. Pathogenic bacteria are found in both Gram-negative and Gram-positive families. Some relevant microbial pathogens include: Gram-positive bacteria (such as *Staphylococcus aureus, Streptococcus pyogenes, Enterococcus* spp., *Clostridium tetani, Listeria monocytogenes* and *Clostridium perfringens*), Gram-negative bacteria (such as *Pseudomonas* spp., *Klebsiella* spp., *Salmonella* spp. and Enterobacteriaceae), and fungi (such as *Candida albicans, Candida parapsilosis, Malassezia furfur, Trichophyton* spp., *Trichoderma*, and *Aspergillus* spp.). Classic skin pathogens include bacteria such as *Staphylococcus aureus*, various *Pseudomonas* spp., and fungi such as *Candida albicans.*

It is accepted knowledge that the use of water as a cleaning agent for medical, household, or industrial use can provide the proper sustenance for the adhesion, proliferation, and colonization of microorganisms. Without the use of sufficient cleaning agents, preservatives, or existing antibacterial agents, a product, or physical surfaces where the product is prepared, may become infected with a variety of microbial organisms. This can ultimately manifest in products that are discolored, odorous, or contain mold or other microorganisms that cause product spoilage, making them unacceptable to consumers. Furthermore, non-visible microbial contamination presents a significant danger of food-borne illness along with a significant risk to consumer health in the case of pathogenic microorganisms. Additionally, the preparation, sterilization, and cleaning of hospital equipment, surgical instruments, and the maintenance of sterility of tubing and materials that interact with blood and other biological fluids poses a significant challenge. Finally, many microbes have become resistant to current antibiotics, allowing them to proliferate despite the use of existing cleaning techniques. New treatments for these resistant microorganisms is desperately needed in the clinical setting.

Many disinfectants pose risk to humans during use, because of tissue-damaging properties. For example, disinfectants containing phenols, chlorine, and other powerful agents can pose risk of damaging skin and mucosal tissue of a consumer during use of the products. Potential toxicity to humans can restrict the types of disinfectants available for use by consumers, and/or the applications for which they can be used.

U.S. Pat. Nos. 6,599,945 and 7,094,809 disclose several hydroxytolan compounds and their use in inhibiting the formation of infectious herpes virus particles or for treating gonorrhea caused by *Neisseria gonorrhoeae*. The compounds outlined in U.S. Pat. Nos. 6,599,945 and 7,094,809 show activity against *Neisseria gonorrhoeae* but failed to show activity against *N. meningitides, E. coli, S. aureus, S. pyogenes, P. aeruginosa*, and *C. albicans*. When the chemical species outlined in this application were applied to *E. coli* and T. *Salmonella*, they exhibited antibacterial activity at much lower dosing concentrations than those described in U.S. Pat. No. 7,094,809. WO2009/126700 discloses the use of similar compounds for skin care, such as UV radiation, and cosmetic uses. And U.S. Pat. No. 8,716,355 (WO2011/0130468) and U.S. Pat. No. 8,680,142 (WO2011/0160301) disclose hydroxytolans for use as anti-tumor agents. WO2016/164531 A2 to applicant BioMendics, discloses certain stilbene and tolan compounds for use as autophagy modulators and for wound care applications. However, the potential utility of these, or other tolans, as antibacterial compounds was unknown until the making of the present invention.

There remains a need for improved anti-microbial agents that can be used to treat physical surfaces and/or biological surfaces.

SUMMARY

The invention relates generally to inhibition or modulation of microbial growth, particularly on biological surfaces like skin, mucosa, wounds, etc., or on physical surfaces such as tables, counters, medical instruments, etc.

In a first aspect, the invention includes a method for inhibiting growth of, or killing, suspected pathogenic microbes on a physical or biological surface, comprising contacting the physical or biological surface with an anti-microbial formulation comprising: an anti-microbially effective amount of a substituted tolan compound having the structure (I):

(I)

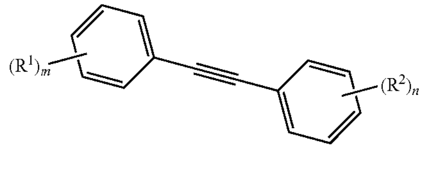

wherein $R^1$ and $R^2$ are independent substituents at any available position of the phenyl rings, and m and n are independently 1, 2, or 3, representing the number of substituents on the phenyl rings, respectively; and wherein each $R^1$, $R^2$, is independently selected from hydroxy, thiol, —($C_1$-$C_6$)alkoxy, —($C_1$-$C_6$)RH" where R is O or S, and $(halo)_p(C_1$-$C_6)$alkyl-, where p is 1, 2, or 3; and salts thereof;

with the proviso that the substituted tolan compound is not 3,4',5-trihydroxytolan.

For example, in some embodiments, the tolan compound is an alkoxytolan, wherein at least one of $R^1$ and $R^2$ substituents is —($C_1$-$C_6$)alkoxy, for example methoxy or ethoxy. In other embodiments, the tolan compound is a hydroxytolan and at least one of $R^1$ and $R^2$ substituents is hydroxy. In other embodiments, the tolan compound is a thiotolan and at least one of $R^1$ and $R^2$ substituents is thiol. In some cases, the tolan compound is a combination of any of the above.

The substituted tolan compound includes at least one $R^1$ and one $R^2$, although they may be the same or different. For example, the tolan compound may be di-substituted, tri-substituted, tetra-substituted or substituted with 5 or 6 substituents, any of which may be the same or different. A few exemplary substituted tolan compounds are provided in Table A, below, including 4,4'-dihydroxytolan, 4,4'-dihydroxy-3-methoxytolan; 4-hydroxy-4'-methoxytolan, 3,5,3', 5' tetrahydroxytolan, 2,4,4'-trimethoxytolan, 3,5,3',5' tetramethoxytolan, and 4-hydroxy-4'-trifluoromethyltolan.

The substituted tolan compound may be present in an amount from about 0.01% to about 30% by weight, based on total weight of the antimicrobial formulation. For example, the tolan compound may be present in an amount from about 0.0001% to about 25% by weight, or from about 0.1% to about 20%, or from about 0.001% to about 20%. The formulation may have a pH of from about 4.1 to about 8.5, and may further include a cleansing agent, preferably one that is substantially free of phenol. In some embodiments, the secondary antimicrobial agent is selected from dichlorophene, hexachlorophene, aldehydes, alcohols, antimicrobial carboxylic acids and derivatives thereof, organometallic compounds, iodine compounds, quaternary ammonium compounds, sulfonium and phosphonium compounds, mercapto compounds and the alkali metal, alkaline earth metal and heavy metal salts thereof, ureas, tribromosalicylanilide, 2-bromo-2-nitro-1,3-dihydroxypropane, dichlorobenzoxazolone, chlorohexidine, isothiazolone, benzisothiazolone derivatives, and combinations of any two or more of these.

The methods and formulation described above may be used to sanitize or disinfect surfaces, by modulating the growth of a microbe or microbes thereon. In some cases, the surface is a physical surface selected from things such as surgical equipment, surgical instruments, and countertops, tubing, syringes, and the like that must be disinfected remain essentially sterile throughout a procedure. In other embodiments, the surface is a physical surface selected from food preparation surfaces selected from cutting boards, countertops, table tops, knives, other utensils, cookware, and the like that might lead to ingestion of unwanted bacteria is not disinfected. In still other embodiments, the surface is a biological surface at a site where skin is not fully intact, such as intravenous lines or ports, arterial lines or ports, PICC lines, catheters, drains, and incision sites. Such biological surfaces may include, e.g., skin, scalp, hair, eyes, mucous membranes, and internal or external orifices.

In another embodiment, the method and formulations may be useful for disrupting a bacterial biofilm in situ.

In some aspects of the method, the suspected pathogenic microbes are Gram negative bacteria, such as the genera of *Neisseria, Chlamydia, Acinetobacter, Haemophilus, Helicobacter, Proteus, Bordetella, Pseudomonas, Salmonella, Enterobacter, Escherichia, Klebsiella, Vibrio*, or *Yersinia*. In other aspects, the suspected pathogenic microbes are Gram positive bacteria, such as *Staphylococcus, Streptococcus, Bacillus, Clostridium, Listeria*, or *Corynebacterium*. In particular embodiments, the suspected pathogenic microbes are those deemed important pathogens due to prevalence or actual or impending resistance to known "last resort" antibiotics, such as methicillin, vancomycin, or carbapenem. These important pathogens include strains of *Acinetobacter baumannii*, (carbapenem-resistant); *Pseudomonas aeruginosa*, (carbapenem-resistant); Enterobacteriaceae, (carbapenem-resistant, ESBL-producing); *Enterococcus faecium*, (vancomycin-resistant); *Staphylococcus aureus*, (methicillin-resistant, vancomycin-intermediate and resistant); *Helicobacter pylori*, (clarithromycin-resistant); *Campylobacter* spp., (fluoroquinolone-resistant); Salmonellae, (fluoroquinolone-resistant); *Neisseria gonorrhoeae*, (cephalosporin-resistant, fluoroquinolone-resistant); and *E. coli* species.

In still other aspects, the suspected pathogenic microbes are fungi, such as those of the *Candida* genus, the *Aspergillus* genus, *Cladosporium* genus, *Epidermophyton* genus, *Microsporum* genus, *Tricophytum* genus, and the *Penicillium* genus.

In another aspect, the invention includes a method for inhibiting or disrupting biofilm formation of a microbe or microbes, comprising contacting the microbe with an antimicrobial formulation comprising:

an effective amount of a substituted tolan compound having the structure (I):

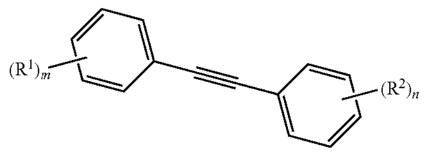

(I)

wherein $R^1$ and $R^2$ are independent substituents at any available position of the phenyl rings, and m and n are independently 1, 2, or 3, representing the number of substituents on the phenyl rings, respectively; and wherein each $R^1$, $R^2$, is independently selected from hydroxy, thiol, —($C_1$-$C_6$)alkoxy, —($C_1$-$C_6$)RH" where R is O or S, and $(halo)_p$($C_1$-$C_6$)alkyl-, where p is 1, 2, or 3; and salts thereof;

with the proviso that the substituted tolan compound is not 3,4',5-trihydroxytolan.

In certain embodiments, the substituted tolan compound is present in the antimicrobial formulation at a concentration ranging from about 0.008 mM to about 1 mM. In certain embodiments, the substituted tolan compound is present in the antimicrobial formulation of about 0.625 mM.

In certain embodiments, the substituted tolan compound is present in the antimicrobial formulation in an amount ranging from about 0.0001% to about 30% by weight, based on total weight of the antimicrobial formulation. In certain embodiments, the substituted tolan compound is present in the antimicrobial formulation in an amount ranging from about 0.01% to about 25% by weight, based on total weight of the antimicrobial formulation. In certain embodiments, the substituted tolan compound is present in the antimicrobial formulation in an amount ranging from about 0.1% to about 30% by weight, based on total weight of the antimicrobial formulation.

In certain embodiments, the antimicrobial formulation is administered from once daily up to about 6 times per day. In certain embodiments, the antimicrobial formulation is administered via an administration route selected from the group consisting of topical, transdermal, oral, nasal, ophthalmic, otic, intravenous, intramuscular, subcutaneous, rectal, and vaginal.

In certain embodiments, the substituted tolan compound comprises 4-hydroxy-4'-methoxytolan. In certain embodiments, the microbe or microbes comprises Gram-positive bacteria. In certain embodiments, the microbe or microbes comprises Gram-negative bacteria. In certain embodiments, the microbe or microbes comprises a fungus. In certain embodiments, the microbe or microbes comprises methicillin resistant *Staphylococcus aureus* (MRSA).

Other embodiments and aspects are described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, incorporated herein and forming a part of the specification, illustrate the present invention in its several aspects and, together with the description, serve to explain the principles of the invention. In the drawings, the thickness of the lines, layers, and regions may be exaggerated for clarity.

FIGS. 6A-6B depict a bar chart (FIG. 6A) and table (FIG. 6B) of the antimicrobial effects of formulations of BM3103 on methicillin-resistant *Staphylococcus aureus* (MRSA USA 300).

DETAILED DESCRIPTION

Figure 1:
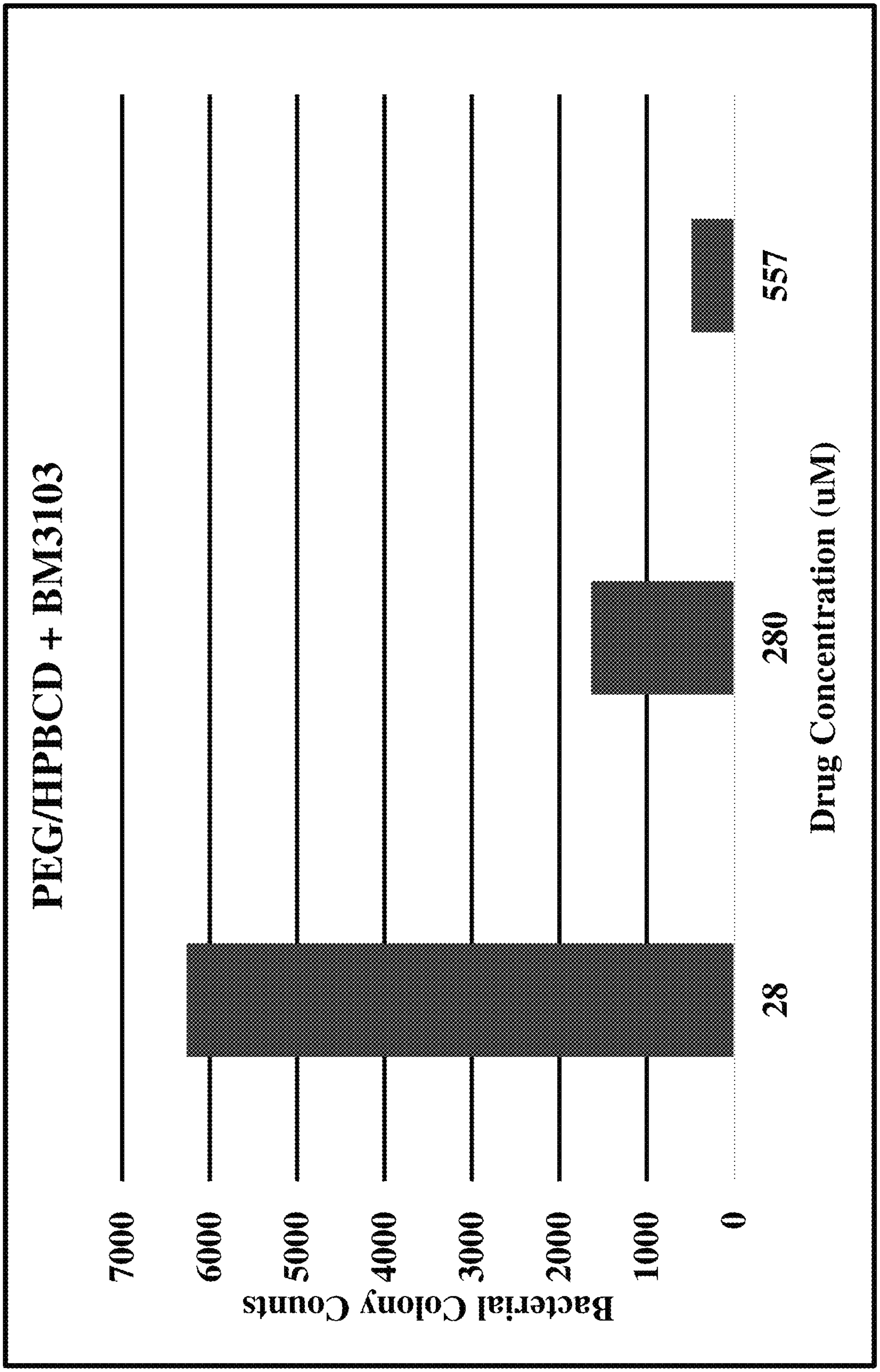
FIG. 1 depicts a bar chart of the antimicrobial effects of the substituted tolan BM3103.

Numerical ranges, measurements and parameters used to characterize the invention—for example, angular degrees, quantities of ingredients, polymer molecular weights, reaction conditions (pH, temperatures, charge levels, etc.), physical dimensions and so forth—are necessarily approximations; and, while reported as precisely as possible, they inherently contain imprecision derived from their respective measurements. Consequently, all numbers expressing ranges of magnitudes as used in the specification and claims are to be understood as being modified in all instances by the term "about." All numerical ranges are understood to include all possible incremental sub-ranges within the outer boundaries of the range. Thus, a range of 30 to 90 units discloses, for example, 35 to 50 units, 45 to 85 units, and 40 to 80 units, etc. Unless otherwise defined, percentages are wt/vol %.

All patents, published patent applications, and non-patent literature references cited herein are incorporated herein by reference in their entirety.

In some aspects, the invention comprises methods of modulating bacterial infection comprising the administration of a single tolan, co-administration of more than one tolan or sequential administration of one tolan followed by a second. The tolan compounds are described in more detail in sections below. They may be given sequentially or concomitantly. The compounds may be administered from once daily up to about 6 times per day, depending on the formulation excipients. Administration routes include topical, transdermal, oral, nasal, ophthalmic, otic, IV, IM, subcutaneous, rectal, and vaginal.

The use of pharmaceutical excipients in the preparation of drug products is generally well understood from pharmaceutical treatises such as Remington's Pharmaceutical Sciences, $18^{th}$ Edition (1990) and its subsequent editions, like Remingtons: The Science and Practice of Pharmacy, $22^{nd}$ edition (2012). Topical formulations may be combined with solvents, emulsifiers, emollients, solvents, etc. into solutions, suspensions, creams, ointments, and hydrogels, among others (Handbook of Formulating Dermal Application, Nava Dayan, 2016; Topical Drug Delivery Formulations, David Osborne & Anton Amann, 1989).

In certain embodiments, the invention involves a formulation containing on a weight percent basis, the active ingredient (tolan compound) may comprise from about 0.01% to about 30% of the formulation. In certain embodiments, the active ingredient (tolan) may comprise from to about 0.1% to about 25% of the formulation. Optimally, the dosage of the antibiotic is between 0.1-20%.

Chemical and Biological Definitions

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein. All references cited herein, including books, journal articles, published U.S. or foreign patent applications, issued U.S. or foreign patents, and any other references, are each incorporated by reference in their entireties, including all data, tables, figures, and text presented in the cited references.

The following terms used throughout this application have the meanings ascribed below.

As used herein, the term "—$(C_1\text{-}C_6)$alkyl" refers to straight-chain and branched non-cyclic saturated hydrocarbons having from 1 to 6 carbon atoms. Representative straight chain —$(C_1\text{-}C_6)$alkyl groups include methyl, -ethyl, -n-propyl, -n-butyl, -n-pentyl, and -n-hexyl.

Representative branched-chain —($C_1$-$C_6$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like. More generally, the subscript refers to the number of carbon atoms in the chain. Thus, the term "—($C_1$-$C_3$)alkyl" refers to straight-chain and branched non-cyclic saturated hydrocarbons having from 1 to 3 carbon atoms.

As used herein, "—($C_1$-$C_6$)alkoxy" means a straight chain or branched non-cyclic hydrocarbon having one or more ether groups and from 1 to 6 carbon atoms. Representative straight chain and branched ($C_1$-$C_6$)alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like. And "—($C_1$-$C_3$)alkoxy" is similarly defined, except having only 1 to 3 carbons.

As used herein, "—($C_1$-$C_6$)RH" where R is O or S means a straight chain or branched non-cyclic alcohol or thiol hydrocarbon having one or more hydroxyl or thiol groups and from 1 to 6 carbon atoms. Representative straight chain and branched —($C_1$-$C_6$)RH include -methanol, methanethiol, ethanol, ethanethiol, n-propanol, isopropanol, n-propanethiol, and the like. And "—($C_1$-$C_3$)RH" is similarly defined, except having only 1 to 3 carbons.

As used herein, the terms "halo" and "halogen" refer to fluoro, chloro, bromo, or iodo.

As used herein, "halo-alkyl" or "$(halo)_p(C_1$-$C_6)$alkyl-" means a ($C_1$-$C_6$) alkyl chain substituted with halo in p locations, where p is 1, 2, or 3. The halo substituents may be substituted on the same or a different carbon in the ($C_1$-$C_6$) alkyl. Representative "$(halo)_p(C_1$-$C_6)$alkyl-" groups include, for example —$CF_3$, —$CH_2CHF_2$, —$CH_2CH_2CH_2Cl$, —$CHBr_2$, —$CHBrCl$, —$CHCFCl$, —$CH_2CHI_2$, —$CH_2CH_2CHClCH_2Br$, and the like.

In some embodiments, there are two phenyl rings shown in a structure and containing substituents $R^1$ and $R^2$. In certain embodiments, there are from one to three $R^1$ substituents, and from one to three $R^2$ substituents on the phenyl rings. In some embodiments, the position of $R^1$ and/or $R^2$ on the phenyl rings is mostly at the para and meta positions, namely the 3, 4, or 5 position on one phenyl ring and the 3', 4', and 5' positions on the other phenyl ring, although it is also possible to have substituents in the ortho position (2, 2', 6, and 6'). There may be one, two, or three $R^2$ substituents on the first phenyl ring, and correspondingly, from one to three $R^Z$ substituents on the second phenyl ring. All permutations within these are possible, for example: one $R^1$ and one $R^1$; two $R^1$ and two $R^1$; three $R^1$ and three $R^1$; one $R^1$ and two $R^2$; one $R^1$ and three $R^2$; two $R^1$ and one $R^2$; two $R^1$ and two $R^2$; two $R^1$ and three $R^2$; three $R^1$ and one $R^2$; or three $R^1$ and two $R^2$. Each $R^1$_$^2$ is independently selected and when two or more are present they may be the same or different. In other words, each occurrence of $R^1$ may be the same or different than another $R^1$ or $R^2$; and each occurrence of $R^2$ may be the same or different than another $R^2$ or $R^1$.

In accordance with the present disclosure, non-limiting examples of some specific substituted tolan antimicrobial compounds are given in Table A.

TABLE A

Representative substituted Tolan antimicrobial compounds

| | The nature and position(s) of $R^1$ and $R^2$ substituents |
|---|---|
| Tolan core | 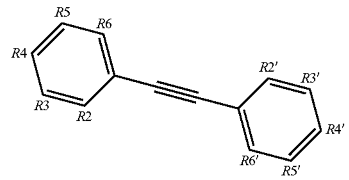 |
| Hydroxy | 3,5-dihydroxytolan; 3,4-dihydroxytolan; 3,4,5-trihydroxytolan; 3,3',4,5'-tetrahydroxytolan; 3,3',4,4'-tetrahydroxytolan; 3,4,4'-trihydroxytolan; 3,3',4'-trihydroxytolan; 2,4,4'-trihydroxytolan; 2,4,2',4'-tetrahydroxytolan; |
| Thiol | 3,5-dihydroxy-4'-thioltolan; 3,4-dihydroxy-4'-thioltolan; 4,5-dihydroxy-4'-thioltolan; 3,4,5-trihydroxy-4'-thioltolan; 3,4'-dithiol-tolan; 4, 4'-dithiol-tolan; |
| Glycosides and mixed | 3,5'-dihydroxy-4'-methoxytolan 5-O-β-D-glucoside; 3',4'-dihydroxy-3-methoxytolan-5-O-β-D-glucoside; 3,4'-dihydroxytolan 5-O-β-D-glucoside; 2,3-dihydroxy-4'-methoxytolan 5-O-β-D-glucoside; 2,3,3'-trihydroxy-4'-methoxytolan 5-O-β-D-glucoside; |
| Haloalkyl | 4-hydroxy-4'-(trifluoro)methyltolan (BM3213); |
| Alkoxy (O-alkyl) and mixed | 3,5,4'-trimethoxytolan; 3,4,4'-trimethoxytolan (BM3303); 4,5,4'-trimethoxytolan; 3,4,5,4'-tetramethoxytolan; 4'-hydroxy-3,5-dimethoxytolan; 4'-hydroxy-3,4-dimethoxytolan; 4'-hydroxy-4,5-dimethoxytolan; 4'-hydroxy-3,4,5-trimethoxytolan; 3,5-dihydroxy-4'-methoxytolan; 4,4'-dimethoxytolan; 3,5,3'-trihydroxy-4'-methoxytolan; 4,4'-dihydroxy-3-methoxytolan; 3,4-dihydroxy-4'-methoxytolan; 3,4-dimethoxytolan; 3,4'-dimethoxytolan; 4-hydroxy-4'-methoxytolan (BM3103); |
| Alcohol and Thiol and mixed | 3,5-dihydroxy-4'-methanoltolan; 3,4-dihydroxy-4'-ethanoltolan; 4,5-dimethanol-4'-thioltolan; 3,5-diethanol-4'-methanoltolan; 3,5-dimethylthiol-4'-hydroxytolan; 3,4-dihydroxy-4'-ethythioltolan; 4,5-dihydroxy-4'-propylthioltolan;3,5-dimethylthiol-4'-methoxytolan; 3,4'-dimethylthiol-tolan; 4,4'-dimethylthiol-tolan |

It can be observed that the tolan compounds described above are generally polar, and have certain electronegative substituents (e.g., —OH, —$OCH_3$, -halo, etc.) at the respective ends. While this is not essential, it may be desirable to provide for a liquid crystal-like behavior for molecules to assume a lyotrophic or partially ordered structure in solution state. Without wishing to be bound by theory, it is believed that this may facilitate their ability to penetrate and disrupt bacterial biofilms that are of a liquid crystalline nature. These compounds act singly and in combinations to prevent microbial colonization of a plant, animal, human, or physical surface where bacteria or other microbes may adhere and colonize. The invention further describes the use of these compounds to be formulated into sprays, coatings, micelles, liposomes, gels, soaps, foams, or creams to prevent or treat a bacterial infection.

Tolan compounds, also referred to herein as substituted tolan compounds, also include salts of the compounds identified above. Tolan compounds, especially those mono or poly-hydroxylated compounds, easily release one or more protons depending on pH to form anions. Such anions may be combined with cations, such as the mono-, di-, and tri-valent cations to form salts. For monovalent cations ($M^+$), a single tolan is linked to form $M^+$tolan$^-$ salts. Similarly, for a divalent cation ($M^{2+}$), two tolan molecules are linked to form $M^{2+}$(tolan$^-$)$_2$ salts; and for a trivalent cation ($M^{3+}$), three tolan molecules are linked to form $M^{+3}$(tolan$^-$)$_3$ salts. The salts are often readily soluble in aqueous media, which may facilitate formulations. Illustrative, but not limiting, cations for tolan salt formation include: $Na^+$ or $K^+$, $Mg^{2+}$, $Mn^{2+}$, $Zn^{2+}$, $Ca^{2+}$, $Cu^+$, $Cu^{2+}Fe^{2+}$, and $Fe^{3+}$. O-glycosides may be formed in a similar manner.

Utility of Antimicrobial Tolans to Disinfectant or Sanitize a Surface

A representative substituted tolan, 4-hydroxy-4'-methoxytolan (BM3103), has been shown to be useful for controlling microbial growth. BM3103 was found to be effective against wild type *E. Coli* where previous data showed 3,5,4'-trihydroxytolan to be ineffective. BM3103 was also shown to disrupt the formation of the bacterial lawn or biofilm. Additionally, BM3103 has been shown to possess significant antimicrobial activity against a series of microorganisms. Further, BM3103 and its related substituted tolans possess low topical toxicity and have broad safety in human and animal skin. This allows them to be utilized to in product formulations with a wide safety profile. Moreover, they can be formulated with other components to provide end products with antimicrobial properties.

Substituted tolans having antimicrobial activity can be formulated and employed as a disinfectant and used on physical or biological surfaces. As used herein, "microbes" is a broad term that encompasses pathogens of all classifications including, in particular, bacteria and fungi (including both their filamentous and yeast forms). Bacteria include both Gram-negative, and Gram-positive staining types, as well as both rod and bacilli morphology. Important bacterial and fungal pathogens, and the applications in which they might be found, include those identified in Table B.

TABLE B

Selected Pathogenic microbes
Microorganisms Relevant for Various Applications

| Microorganism | Potential Application |
|---|---|
| Fungi | |
| *Aspergillis Niger*, *Aspergillius flavus*, *Aspergillius parasiticus*, *Aspergillius oryzae*, *Aspergillius* sp., *Cladosporium*, *Penicillium chrysogenum*, *Margarinomyces fasciculatis*, *Stemphylium congestum*, *Trichiderma viride* | Slime formation |
| *Dermatophytic Fungi*: *Epidermophytum* sp., *Microsporum* sp., *Tricophytum* sp. | Cosmetics<br>Personal Care Products<br>Skin Care Products |
| *Spoilage fungi*: *Aspergillus* sp., *Candida* sp., *Penicilliumm* sp. *Alicyclobacillus* sp., *Candida albicans*, other *Candida* sp., *Pullulaeria pullelelus*, *Rhotorula* sp., and *Saccharomyces* sp. *Pityrosporum ovale* | Cosmetics<br>Consumer products<br>Personal Care Products |
| Bacteria | |
| *Acremonium strictum*, *Bacillus* sp., *Citrobacter freundii*, *E. Coli*, Fusarium solani, *Geotrichum candidum*, *Penicillium* sp., *proteus mirabilis*, *Pseudomonas* sp., *Pseudomonasstuizeri* | Consumer Products |
| Gram Positive bacteria: *Corynebacterium*, *Staphylococcus*, *Streptococcus bacillus.* | Personal Care Products<br>Skin Care Products |
| Gram Negative bacteria: *E. Coli*, *Enterobacter aerogenes*, *Flavobacteria*, *Klebsiella*, *Proteus*, *Pseudomonas*, *Salmonella*, *Serratia marcescens.* | Personal Care Products<br>Skin Care Products |

As used herein "antimicrobial" is a broad term that encompasses both the killing of microbes (e.g., bactericidal or fungicidal) and the inhibition of the growth of microbes (e.g., bacteriostatic or fungistatic). Often in biological systems, a static agent is sufficient to prevent growth while the body rids itself of the infectious organism through natural means. As used herein, the term "disinfect" means the elimination of many or all undesirable (e.g., pathogenic) microorganisms in an environment (e.g., a surface). As used herein, the term "sanitize" means the reduction of contaminants in the inanimate environment to levels considered safe, according to public health ordinance, or that reduces the bacterial population by significant numbers.

Given the properties of BM3103 and related substituted tolan antimicrobials, the compounds may be used as an active ingredient or auxiliary agent that can be combined with a solvent to reach a desired concentration providing the final product with the desired antimicrobial, disinfectant, or sanitizing activity. Likewise, the compounds can be combined with components typically found in consumer products such as detergents, soaps, surfactants, emollients, and the like.

In certain aspects, the antibacterial agents described as tolans may be combined into a composition of one or more antimicrobial agents. This composition may then be combined with other ingredients to create a broad-spectrum antimicrobial, disinfectant, or sanitizing agent. Furthermore, in certain aspects, the antibacterial agents described as tolans may be combined with one or more antibiotics in the same formulation in a combination treatment with multiple formulations. Suitable antibiotics may include aminoglycosides, ansamycins, carbacephems, flagyl (metronidazole), neomycin sulfate, carbapenems, cephalosporins, glycopeptides, macrolides, monobactams, penicillins, polypeptides, polymyxin, quinolones, sulfonamides, and tetracyclines. Examples of suitable antibiotics include, but are not limited to: clindamycin, tigecycline, vancomycin, ciprofloxacin, ofloxacin, sulfamethoxazole, trimethoprim/sulfamethoxazole, amoxicillin, penicillin V, penicillin G, procaine penicillin, benzathine penicillin, carbencillin, mezlocillin, ampicillin, piperacillin, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin (rifampin in US), thiamphenicol, timidazole, dapsone, lofazimine, bacampicillin, tiearcillin, ticarcillin, piperacillin/tazobactam, aztreonam, cefotetan, loracarbef, mefoxin, merrem, levofloxacin, lomefioxacin, primaxim, cycloserine, kanamycin, dicloxacillin, demeclocycline, minocycline, doxycycline, oxytetracycline, tobramycin, gentamicin, neomycin, amikacin, craramyein, nebcin, erythromycin/sulfisoxazole, netromycin, streptomycin, tobramycin, cefotaxime, cefuroxime, cefazoline, ceffibuten, ceffizoxime, cefaclor, cefopoerazone, cefprozil, cefadroxil monohydrate, ceftazidime, trimethoprim/sulfamethoxazole, cephalexin, cefazolin, cefamandole nafate, cefepime, cefonicid, sulfadiazine, norfloxacin, enoxacin, cefdinir, seromycin, ceftriaxone, cefixime, ceftazidime, clarithromycin, dirithromycin, methenamine, ethionamide, trovafioxacin, sparfloxacin, interfon-α, indinavir, ganciclovir, foscamet, lamivudine, famciclovir, rimantadine, zalcitabine, interferon-β, saquinavir, ritonavir, ribavirin, erythromycin, troleandomycin, azithromycin, eliiidamycin, colistin, amphotericin B, flucytosine, fluconazole, griseofulvin, grepafloxacin, ultramicrosize griseofulvin, terbinafine, ketoconazole, clotrimazole, dapsone, delavirdine, ziduvudine, amantadine, palivizumab, valacyclovir, didanosine, nelfinavir, nevirapine, ribavirin, cidofovir, pyrimethamine, metronidazole, furazolidone, atovaquone, stavudine, lamiduvine, acyclovir, mionazole, itraconazole, chloroquine, pyrimethamine, mefloquine, hydroxychloroquine, capreomycin, permethrin, crotamiton, lindane, fluoro-uracil, ethambutol, rifabutin, isoniazid, aminosalicyclic acid, rifapentine, pyrazinamide, coenzoyl peroxide, chlorhexidine gluconate, sodium oxychlorosene, benzoyl peroxide, rifampin, rifampin/isoniazid, rifampin/isoniazid/pyrazinamide, nitrofurantoin, linezolid, nitrofurantoin, fosfomycin, nalidixic acid, atropine, oxytetracycline/sulfamethizole/phenazopyridine, chloramphenical, neomycin/polymyxin, tfimetorpim/polythyxin, tobramycin/dexamethasone, vidatabine, ciprofloxacin, ofioxacin, sulfacetamide, povidoneodine, gentamicin, nystatin, chloramphenicol, bacitracin, sulconazole, terbinafine, tetrachlorosalicylanilide, metronidazole, metromdazole, ciclopiroxolamine, clotrimazole, clotrimazole/betamethasone, butenafine, clotrimazole, nattifine, oxiconazole, selenium, econazole, penciclovir, or a pharmaceutically acceptable salt thereof. A combination treatment may involve simultaneous administration of the tolan compound and the antibiotic, or may involve sequential administration of the tolan compound and the antibiotic.

Furthermore, the invention provides a method of treating a surface wherein the surface treatment composition is a substantially phenol free antimicrobial, disinfectant, or sanitizing agent, where the antimicrobial agent is present in a sufficient amount to control microbial growth.

In some aspects, the broad-spectrum activity of the antimicrobial agents described herein can function to reduce the likelihood of biofilm formation and/or work to disrupt biofilms in various states of formation. Microorganisms form biofilms on biological and non-biological surfaces providing them with a strong ecological advantage. Generally, biofilm formation provides an alternative protected existence for microbial organisms. Within the fully-formed biofilm the bacteria are protected by a self-produced extracellular matrix that accounts for ninety percent of the biomass. Once formed, the biofilm provides a hydrated and high tensile strength shelter allowing for the exchange of genetic material. The biofilm also provides protection against desiccation, predation, oxidation, radiation, and penetration of antibiotics, disinfectants, or sanitizers. A review on biofilms, Kostakioti M., et al. (2013) *Bacterial biofilms: development, dispersal, and therapeutic strategies in the dawn of the postantibiotic era*. Cold Spring Harbor Perspectives in Medicine. April 1; 3(4): a010306. is incorporated herein in its entirety. The extracellular matrix produced by bacteria such as *Pseudomonas aeruginosa* self-assembles into a liquid crystalline matrix through entropic interactions between polymers and filamentous Pf bacteriophages, which are long negatively charged filaments. This liquid crystalline structure enhances biofilm function by increasing adhesion and tolerance to desiccation and antibiotics (Secor, P. R. et. al. (2015). Filamentous Bacteriophage Promote Biofilm Assembly and Function. Cell Host Microbe. November 11; 18(5): 549-559.).

Tolans may be synthesized using the general procedures described in U.S. Pat. No. 6,599,945 B2 of Docherty & Tsai, incorporated herein by reference for all purposes. Other methods of synthesizing tolan compounds may be possible and are entirely encompassed within the present disclosure.

EXAMPLES

Examples 1-5: Dose Range Finding Colony Forming Assay

A series of dose range finding assays were performed with five bacterial strains, *S. typhimurium* TA97a, TA98, TA100, TA1535, and *E. coli* WP2 uvrA pKM101, with and without metabolic activation at three plates per dose. The following doses, along with positive and negative controls, were tested: 5000, 2500, 1250, 500, 250, 125, 50, 20, 10, 5, 2, 1, and 0.2 μg/plate. The plates were evaluated for toxicity (a decrease in plate counts with increasing dose and/or a visible thinning of the background lawn) and for precipitation of the test article. Metabolic activation was included in some samples by adding phenobarbital/benzoflavone-induced rat liver S9 fractions with cofactors (S9 mix). Prior to use, freshly thawed aliquots of rat liver S9 were mixed with a sterile cofactor mix. The S9 mix contains a 10% liver S9 concentration and was refrigerated or stored on ice until used. When testing with metabolic activation, the S9 mix was used in the assay tube in place of phosphate buffer.

Dosing formulations were prepared to deliver all doses in a constant volume of 0.1 mL. The highest dose was prepared from test article weighed to the nearest 0.1 mg and the remaining formulations were prepared as serial dilutions from the high dose stock formulation. Using a permanent marking pen or computer printed labels, assay plates were labeled with the project and study numbers and the date. Assay plates and tubes were labeled with a unique identifier, which was used to match the assay tubes with the properly identified minimal glucose agar plate.

The pre-incubation method was used to perform the assay. The assay mix consisted of 0.1 mL of the test article formulation or control article, 0.5 mL S9 mix or phosphate buffer, and 0.1 mL of bacterial culture. Assay tubes were incubated at 37±1° C. with gentle agitation for 20±1 minutes, then 2.0-2.5 mL top agar was added to the assay mix and the top agar/assay mix poured onto appropriately labeled minimal glucose agar plates. Once the top agar hardened, the plates were inverted and incubated at 37±1° C. for 48±2 hours. Plates were counted with the Sorcerer (v. 2.2)/Ames Study Manager (v. 1.2.4) system from Perceptive Instruments (Suffolk, UK). With this system, plate counts are automatically transferred from the plate imager (Sorcerer) to a Study Manager spreadsheet, and the data are stored in a secure manner on an Oracle database. Some plates were hand counted, e.g., if sample precipitate interferes with automatic counting or toxicity results in the formation of microcolonies, in which case, counts for these plates were entered into the spreadsheet manually. Plates were scored also with the extent of colonization by a post fix code. The data are in Tables 1-5, below. Abbreviations used throughout the tables are:

| Positive Controls | | Plate Postfix Codes | |
|---|---|---|---|
| $NaN_3$ | Sodium Azide | A | Lawn absent |
| BAP_Moltox | Benzo(a) pyrene_Moltox | E | Enhanced lawn |
| 4NQO | 4-nitroquinoline N-oxide | P | Precipitate |
| 2A | 2-Aminoanthracene | S | Sparse lawn |
| | Ethanol | T | Toxicity |
| | | # | (e.g. 0, 6, 56, etc. counts) |

TABLE 1

| Strain TA97a with metabolic activation | | | | |
|---|---|---|---|---|
| Strain | Compound | Dose level/plate | Colony forming units/plate | Individual colony counts |
| TA97a | BM3103 | 5000 μg | 0.0 | 0 P |
| | | 2500 μg | 0.0 | 0AP |
| | | 1250 μg | 0.0 | 0 A P |
| | | 500 μg | 0.0 | 0 A |
| | | 250 μg | 0.0 | 0 A |

TABLE 1-continued

| Strain TA97a with metabolic activation | | | | |
|---|---|---|---|---|
| Strain | Compound | Dose level/plate | Colony forming units/plate | Individual colony counts |
| | | 125 µg | 0.0 | 0 A |
| | | 50 µg | 0.0 | 0 |
| | | 20 µg | 0.0 | 0 A |
| | | 10 µg | 77.0 | 77.0 |
| | | 5 µg | 78.0 | 78 |
| | | 2 µg | 78.0 | 78 |
| | | 1 µg | 122.0 | 122 |
| | | 0.2 µg | 89.0 | 89 |
| | Ethanol | | 101.7 | 100, 94, 111 |
| | 2A | 2.5 µg | 3241.3 | 3115, 3093, 3516 |

TABLE 2

| Strain TA100 with metabolic activation | | | | |
|---|---|---|---|---|
| Strain | Compound | Dose level/plate | Colony forming units/plate | Individual colony counts |
| TA100 | BM3103 | 5000 µg | 0.0 | 0 A P |
| | | 2500 µg | 0.0 | 0 A P |
| | | 1250 µg | 0.0 | 0 A P |
| | | 500 µg | 0.0 | 0 A |
| | | 250 µg | 0.0 | 0 A |
| | | 125 µg | 0.0 | 0 A |
| | | 50 µg | 0.0 | 0 A |
| | | 20 µg | 54.0 | 54 |
| | | 10 µg | 38.0 | 38 S T |
| | | 5 µg | 74.0 | 74 |
| | | 2 µg | 36.0 | 360 T |
| | | 1 µg | 56.0 | 56 |
| | | 0.2 µg | 78 | 78 |
| | Ethanol | | 75.7 | 69, 84, 74 |
| | BAP_Moltox | 2 µg | 806.0 | 703, 721, 994 |

TABLE 3

| Strain TA98 with metabolic activation | | | | |
|---|---|---|---|---|
| Strain | Compound | Dose level/plate | Colony forming units/plate | Individual colony counts |
| TA98 | BM3103 | 5000 µg | 0.0 | 0 A P |
| | | 2500 µg | 0.0 | 0 A P |
| | | 1250 µg | 0.0 | 0 A P |
| | | 500 µg | 0.0 | 0 A P |
| | | 250 µg | 0.0 | 0 A |
| | | 125 µg | 0.0 | 0 A |
| | | 50 µg | 0.0 | 0 A |
| | | 20 µg | 0.0 | 0 A |
| | | 10 µg | 16.0 | 16E |
| | | 5 µg | 16.0 | 16 |
| | | 2 µg | 18.0 | 18 |
| | | 1 µg | 8.0 | 8 |
| | Ethanol | | 16.7 | 16, 22, 12 |
| | 2A | 2 µg | 2315.0 | 2664, 1955, 2326 |

TABLE 4

| Strain TA1535 without metabolic activation | | | | |
|---|---|---|---|---|
| Strain | Compound | Dose level/plate | Colony forming units/plate | Individual colony counts |
| TA1535 | BM3103 | 5000 µg | 0.0 | 0 A P |
| | | 2500 µg | 0.0 | 0 A P |
| | | 1250 µg | 0.0 | 0 A P |
| | | 500 µg | 0.0 | 0 A |
| | | 250 µg | 0.0 | 0 A |

TABLE 4-continued

| Strain TA1535 without metabolic activation | | | | |
|---|---|---|---|---|
| Strain | Compound | Dose level/plate | Colony forming units/plate | Individual colony counts |
| | | 125 µg | 0.0 | 0 A |
| | | 50 µg | 0.0 | 0 A |
| | | 20 µg | 0.0 | 0 A |
| | | 10 µg | 0.0 | 0 A T |
| | | 5 µg | 6.0 | 6 |
| | | 2 µg | 10.0 | 10 |
| | | 1 µg | 11.0 | 11 |
| | | 0.2 µg | 12.0 | 12 |
| | Ethanol | | 11.7 | 14, 9, 12 |
| | NaN3 | 1 µg | 714.7 | 661, 702, 781 |

TABLE 5

| Strain WP2 uvrA pkM101 without metabolic activation | | | | |
|---|---|---|---|---|
| Strain | Compound | Dose level/plate | Colony forming units/plate | Individual colony counts |
| WP2 uvrA pkM101 | BM3103 | 5000 µg | 0.0 | 0 A P |
| | | 2500 µg | 0.0 | 0 A P |
| | | 1250 µg | 0.0 | 0 A |
| | | 500 µg | 0.0 | 0 A P |
| | | 250 µg | 0.0 | 0 A P |
| | | 125 µg | 0.0 | 0 |
| | | 50 µg | 14.0 | 14 |
| | | 20 µg | 138.0 | 138 |
| | Ethanol | | 151.0 | 153, 142, 158 |
| | 4NQO | 0.25 µg | 2950.3 | 2987, 2951, 2913 |

Examples 6-9: Bacterial Colony Forming Assay

NEB 5 α competent *E. coli* were retrieved from frozen cultures and grown overnight in a bacterial incubator at 37° C. Proliferating cultures of bacteria were used in a colony forming assay by adding 25 µL of bacteria from the overnight culture to 10 mL of fresh Lysogeny Broth (LB; Bertani, G. (2004). "*Lysogeny at mid-twentieth century: P1, P2, and other experimental systems*". *Journal of Bacteriology.* 186 (3): 595-600. PMC 321500. PMID 14729683. doi:10.1128/JR.186.3.595-600.2004). 1 mL of this diluted bacteria was added to various dilutions of formulations of substituted tolan compounds as described in Table C, below and in charts of the corresponding Figures.

TABLE C

| Formulations of Tolan Compounds | | | |
|---|---|---|---|
| Example | Tolan* Compound | Formulation | Data Figure |
| 6 | BM3103 | 30% PEG-400 and up to 28% HPβCD (hydroxypropyl-β-cyclodextrin) in water with serial dilutions of compound BM3103 mixed into a 70% volume/volume alcohol gel | 1 |
| 7 | BM3103 | 70% volume/volume alcohol gel | 2 |
| 8 | BM3213 | 70% volume/volume alcohol gel | 3 |
| 9 | BM3303 | 70% volume/volume alcohol gel | 4 |

*Refer to Table A for compound identification

One mL of each formulation was mixed with 1 mL of diluted bacteria in LB and put onto agar plates. Alcohol gels were allowed to dry and incubated overnight for 16-18 hrs. Control plates consisted of 2 mL alcohol gel plus 1 mL diluted bacteria, resulting in a colony count of less than 10 colonies, a 1 mL alcohol gel plus 1 mL diluted bacteria, resulting in a partial lawn of bacteria (colonies were too close to count appropriately), 1 mL diluted bacteria alone, resulting in a full lawn of bacteria (no distinguishable colonies), and an appropriate dilution of PEG-400 and HPβCD into 1 mL of alcohol gel plus 1 mL diluted bacteria, resulting in a lawn of bacteria. Plate area was then selected and the Image J colony counter was used to obtain colony counts (Size (pixels squared) 5-1000 and circularity 0.5-1).

Figure 2:
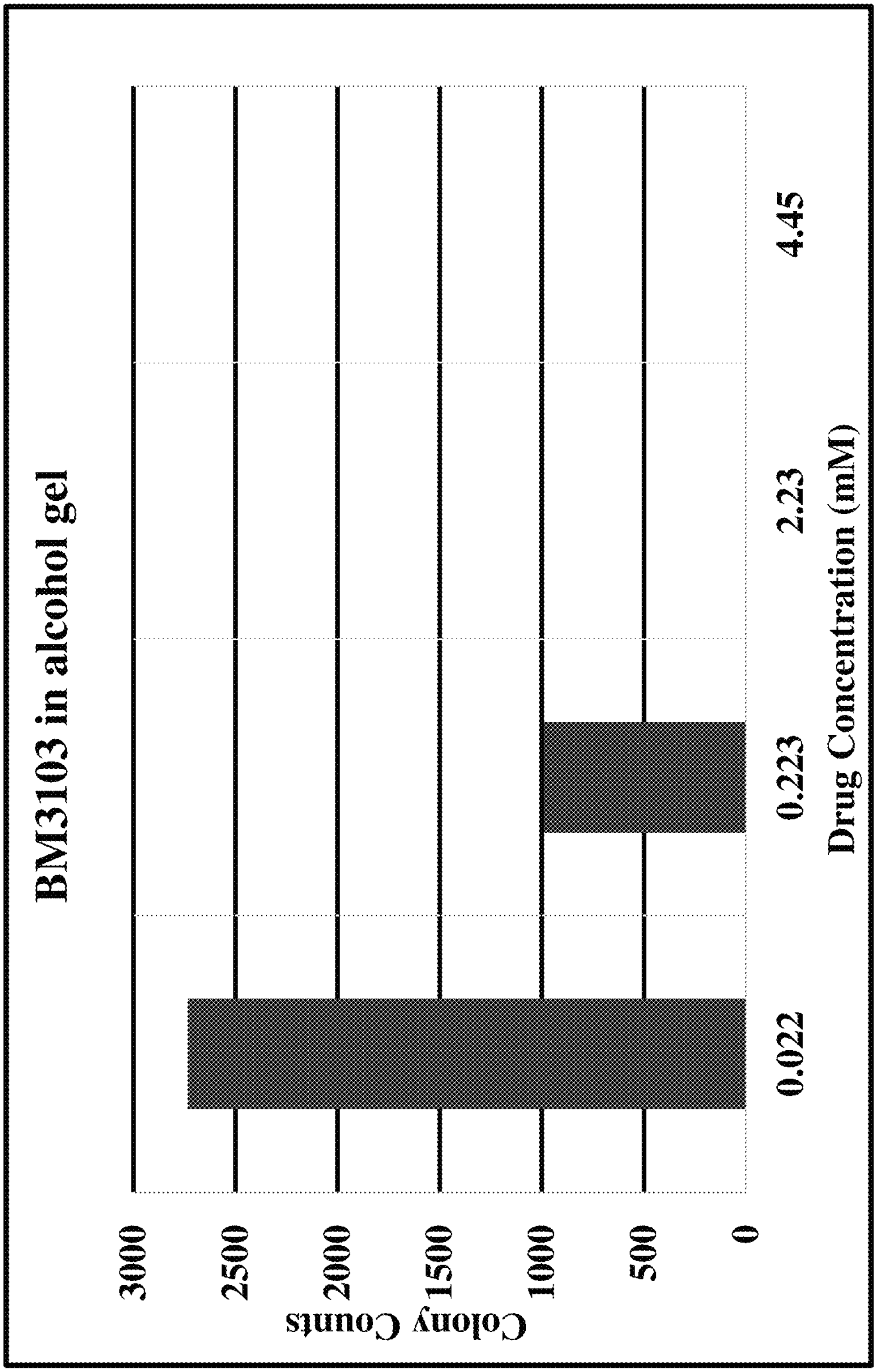
FIG. 2 depicts a bar chart of the antimicrobial effects of the substituted tolan BM3103.
Figure 3:
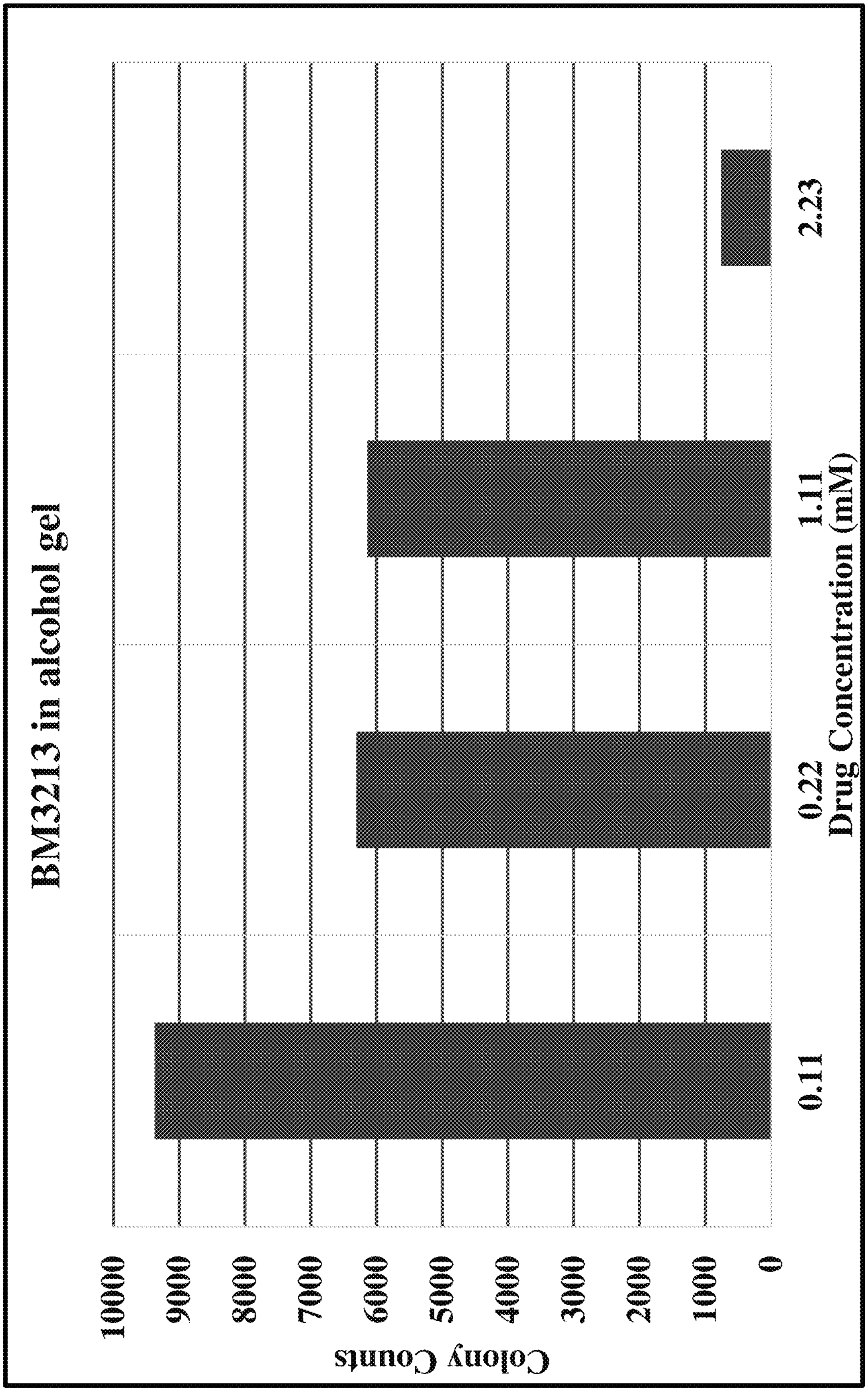
FIG. 3 depicts a bar chart of the antimicrobial effects of the substituted tolan BM3213.
Figure 4:
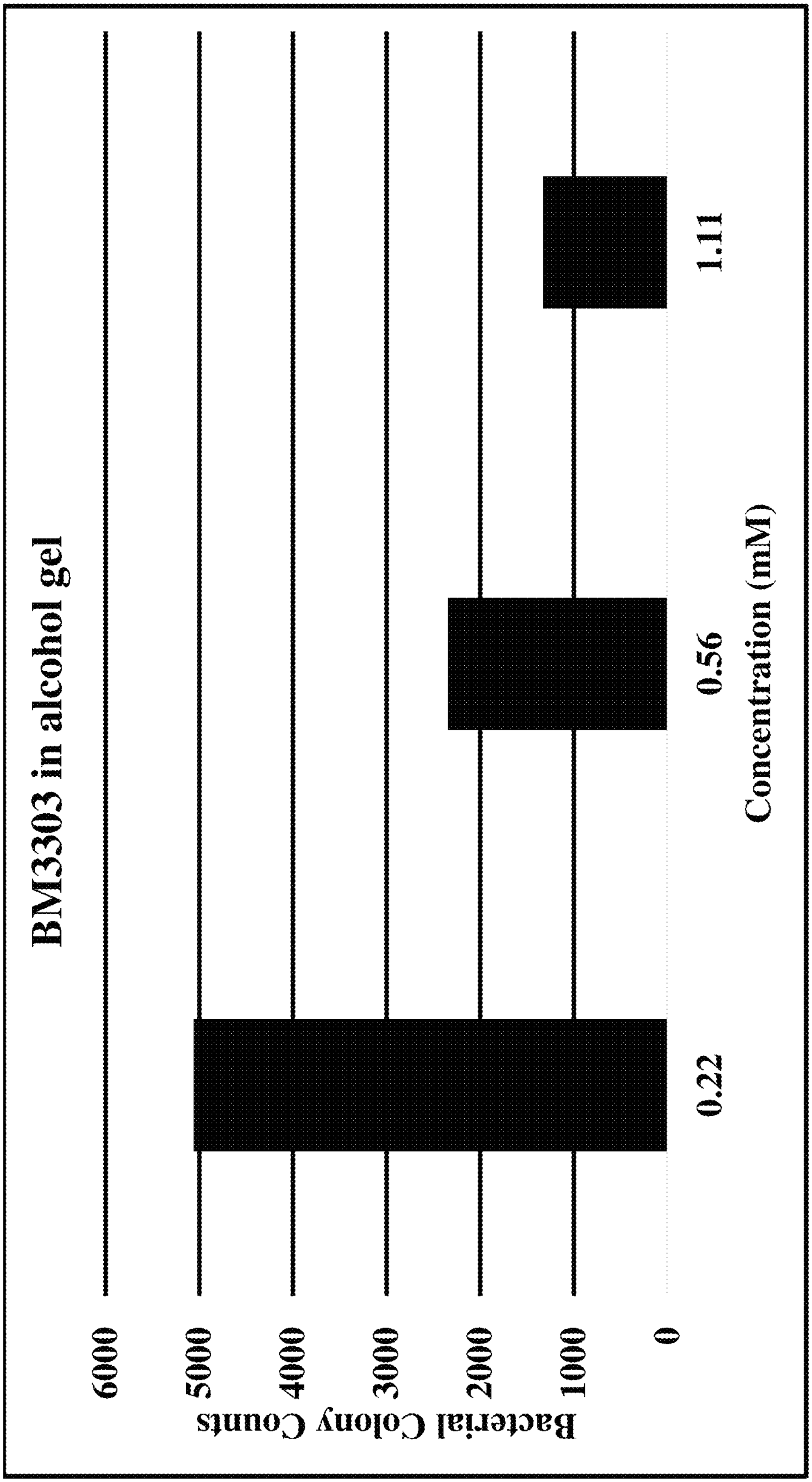
FIG. 4 depicts a bar chart of the antimicrobial effects of the substituted tolan BM3303.

As seen in FIG. 1, a 280 μM (62.5 μg/mL) dilution of BM3103 reduced the *E. coli* colony count considerably and the 557 μM (125 μg/mL) dilution reduced colonization even more. FIG. 2 shows that the alcohol gel formulations of BM3103 at concentrations of 2.23 mM (500 μg/mL) and 4.45 mM (1000 μg/mL) both inhibited *E. coli* growth completely. In FIG. 3, BM3213 in alcohol gel was very inhibitory to *E. coli* at concentrations of 2.23 mM, but less so at concentrations 10 fold diluted. Finally, BM3303 in alcohol gel showed dose dependent inhibitory effects. FIG. 4 shows BM3303 in alcohol gel was an inhibitor to *E. coli* at concentrations of 1.11 mM, but less so at concentrations 10-fold diluted. Finally, BM3303 in alcohol gel showed dose dependent inhibitory effects.

Examples 10-12: MRSA, *Pseudomonas aeruginosa*, and *Candida albicans*

Materials

A fresh culture of pathogenic isolate was used in these examples. The bacterial strains used were Methicillin Resistant *Staphylococcus aureus* (MRSA USA 300), *Pseudomonas aeruginosa* ATCC 27312, and *Candida albicans* ATCC 64550.

Figure 5:
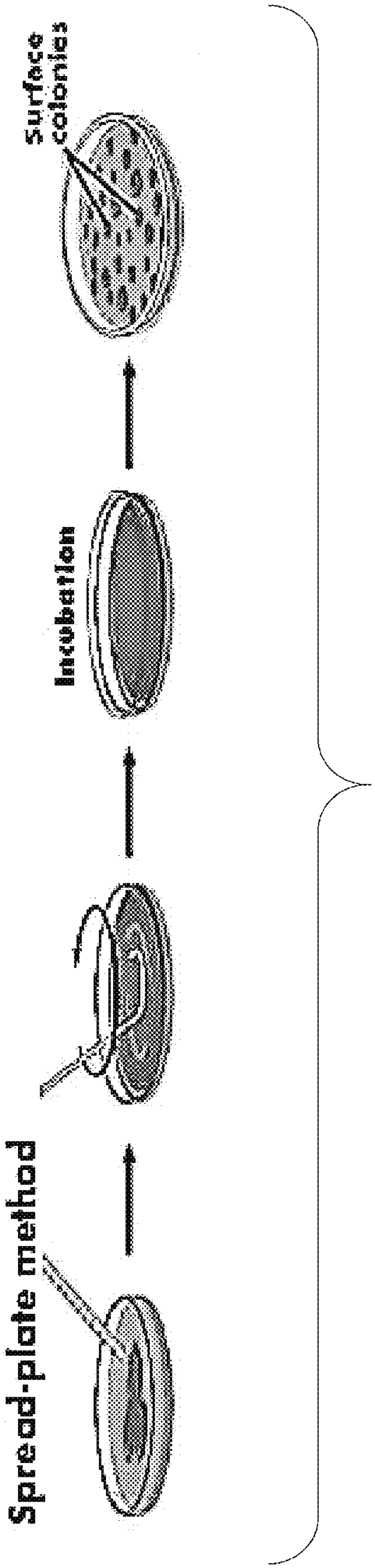
FIG. 5 depicts the methodology used in Examples 10-12.

FIG. 5 illustrates the spread plate method used in these examples. In sum, agar plates were made, bacteria were diluted to $10^6$ or $10^8$ CFU/mL, bacteria and drug were mixed together and then plated. Glass spreading beads were used because they give a better bacterial spread. Plates were incubated for 24 hrs then the colonies that formed were counted.

Proliferating cultures of Methicillin Resistant *Staphylococcus aureus* (MRSA, USA 300) were used in a colony forming assay. Freeze-dried bacteria culture of MRSA was recovered by swabbing a 3-cm diameter growth area and resuspending it to obtain a final inoculum suspension of approximately $10^8$ CFU/mL. The concentration was confirmed using historical optical density measurements. The total compound BM3103 was suspended in a 70% v/v alcohol gel formulation (Formulation A) before the introduction of bacteria, with the vehicle consisting of solely the 70% v/v alcohol gel. MRSA at $10^8$ CFU/mL was challenged with equal parts of a high, medium, and low dose of BM3103, vehicle formulation, positive control (Tobramycin, 600 μg/mL), or untreated control (phosphate buffered saline). The inoculum was plated on Tryptic Soy Broth plates at 37° C. for 24 h. Plates were photographed and counted. The treatment for each experiment was done in triplicate, and the experiment was repeated three times, for a total of 9 plates per group.

Figure 6A:
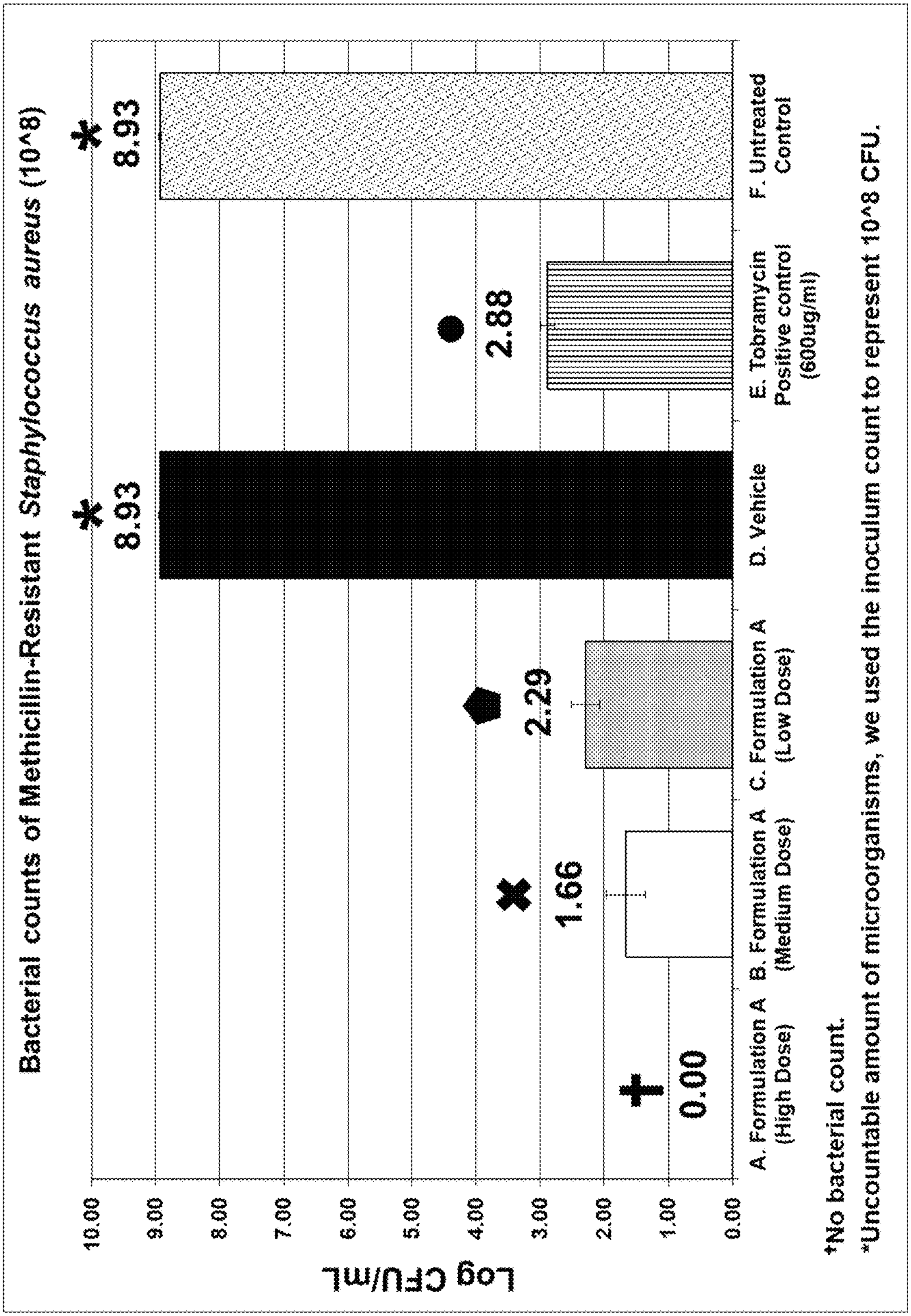

Colony counts for each treatment were tabulated and the Log of the colony forming units/mL (Log CFU/mL) was determined. The mean and standard deviation of the Log CFU/mL were calculated for each treatment. A one-way analysis of variance was performed at a 95% confidence interval. As seen in FIGS. 6A-6B, the positive control of Tobramycin reduced the MRSA USA 300 counts by 6-fold reduction when compared to the untreated control. The low dose of BM3103 (0.05% w/v, 2 mM) reduced the counts significantly by over 6-fold when compared to the vehicle (35% v/v, alcohol) and untreated controls. The medium dose (0.25% w/v, 11 mM) reduced counts significantly by 7-fold reduction compared to the vehicle and untreated control, and the high dose of BM3103 (0.5% w/v, 22 mM) reduced the MRSA USA 300 counts completely by approximately 8-fold. All three doses of BM3103 showed significantly greater reduction in MRSA USA 300 counts when compared to the positive control and showed a dose dependent inhibitory effect.

Proliferating cultures of *Pseudomonas aeruginosa* (PA, ATCC 27312) and *Candida albicans* (CA, ATCC 64550) were used in a colony forming assay. Freeze-dried bacteria cultures were recovered by swabbing a 3-cm diameter growth area and resuspending it to obtain a final inoculum suspension of approximately $10^6$ CFU/mL. The concentration was confirmed using historical optical density measurements. Before bacteria challenge, the tolan compound BM3103 was suspended in 100% diethylene glycol monoethyl ether (Formulation C) with vehicle control consisting solely of the diethylene glycol monoethyl ether. Before plating, 100 μL of the final inoculum ($10^6$ CFU/mL) was mixed with 200 μL LB broth and 200 μL of BM3103 doses, vehicle, positive control (Tobramycin, 12 μg/mL for PA and 160 μg/mL for CA), or untreated control (phosphate buffered saline). The final plating concentration for the high, middle, and low BM3103 doses were 0.5%, 0.25%, and 0.1% w/v (22 mM, 11 mM, and 4 mM), respectively. The inoculum was plated on agar with centrimide and nalidixate (CN) supplement for PA (though sodium nalidixate or nalixic acid could also be used), and on Tryptic Soy Broth plates for CA experiments, at 37° C. for 24 h. Plates were photographed and counted. The experiment was done in triplicate.

Figure 7:
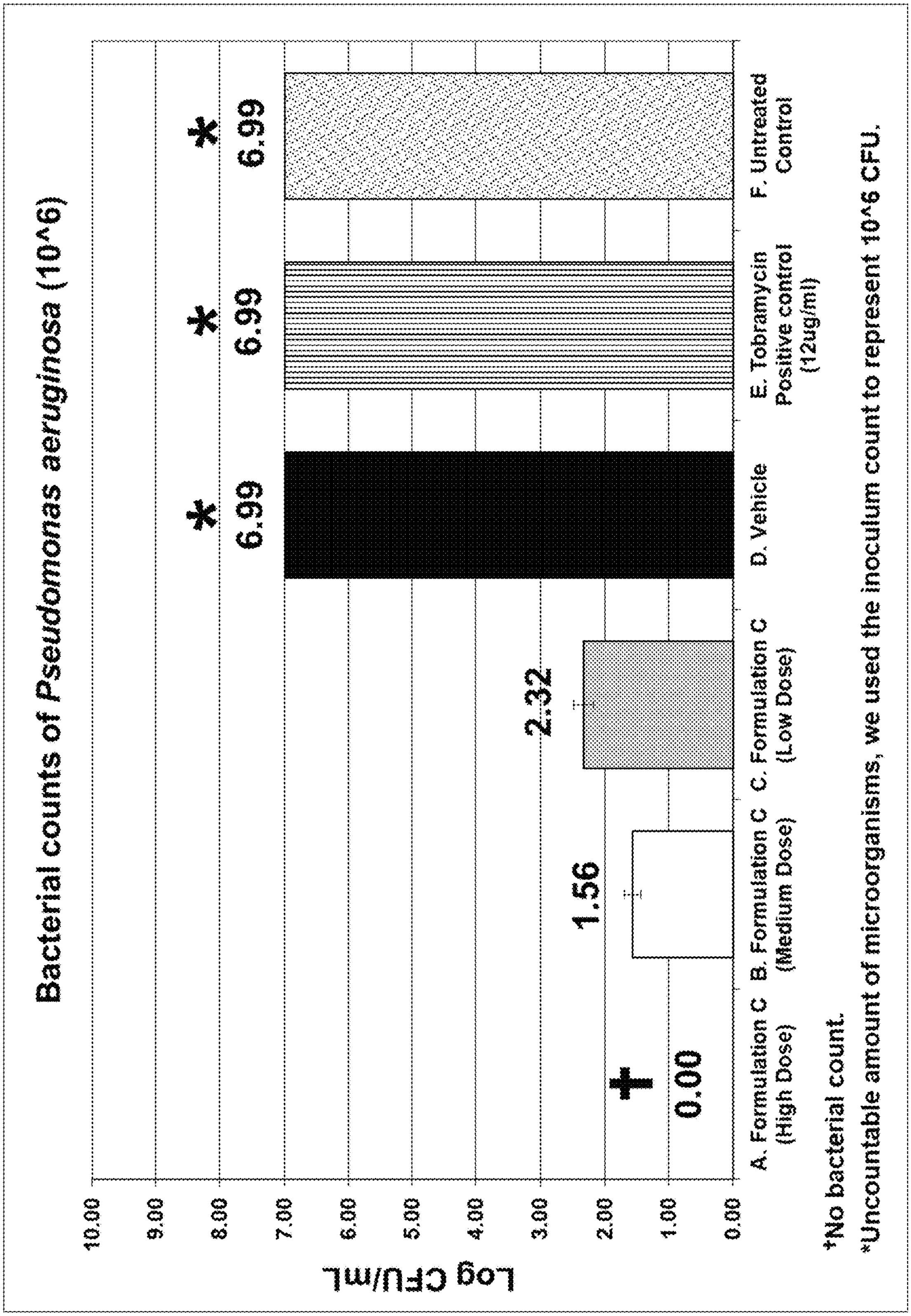
FIG. 7 depicts a bar chart of the antimicrobial effects of formulations of BM3103 on *Pseudomonas aeruginosa.*

Colony counts for each treatment were tabulated and the Log of the colony forming units/mL (Log CFU/mL) were determined. The mean and standard deviation of the Log CFU/mL were calculated for each treatment. FIG. 7 shows the Log CFU/mL bacterial counts of PA. There were no bacteria colonies of PA found on the high dose, BM3103 (0.5% w/v, 22 mM), plates. The medium and low dose groups reduced PA counts when compared to the vehicle, Tobramycin, and untreated control groups by about 5-fold. BM3103 showed a dose dependent inhibitory effect on PA bacterial counts.

Figure 8:
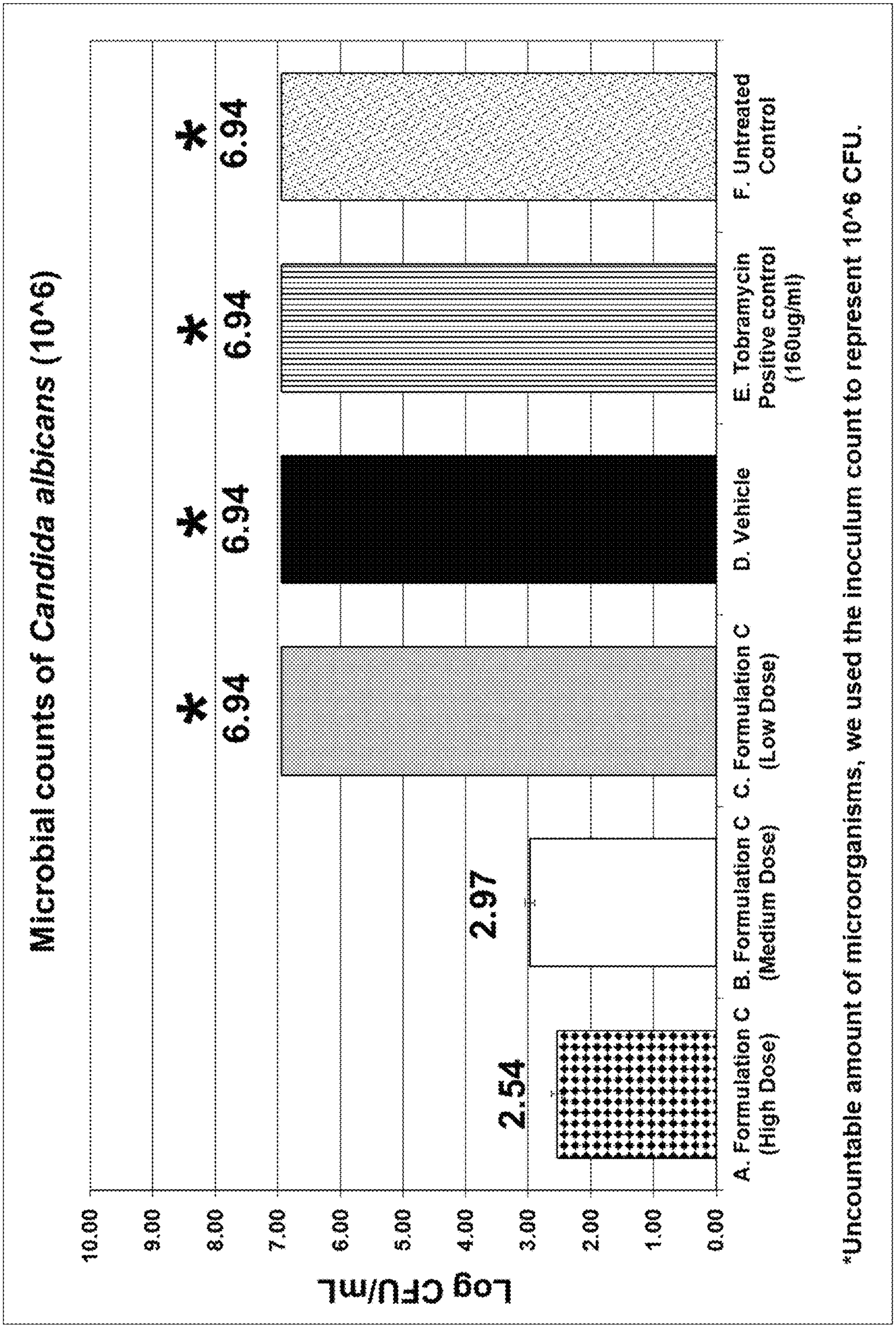
FIG. 8 depicts a bar chart of the antimicrobial effects of formulations of BM3103 on *Candida albicans.*

FIG. 8 shows the Log CFU/mL bacterial counts of CA. The high and medium dose groups reduced CA counts when compared to the low dose, vehicle, Tobramycin, and untreated control groups by about 4-fold.

Example 13: MRSA USA 400

MRSA Inoculum

Proliferating cultures of Methicillin Resistant *Staphylococcus aureus* (MRSA, USA 400) were used in a colony forming assay. Frozen stock cultures of MRSA USA 400 were thawed and grown overnight in tryptic soy broth (TSB) with shaking at 37° C. The overnight culture (0.5-1.0 mL) was added to 100 mL TSB and grown at 37° C. with shaking and monitored for an optical density of 0.55-0.60 in order to obtain a final inoculum suspension of approximately $10^8$ CFU/mL.

Alcohol Gel Formulation

BM3103 was suspended into a 70% v/v alcohol gel formulation to acquire the desired % w/v tested within the example. Each concentration was vortexed thoroughly until dissolved. Initial tested concentrations of BM3103 were 1, 0.5, and 0.1% w/v. These concentrations and the alcohol gel vehicle were mixed with equal parts of the $10^8$ CFU/mL inoculum to obtain a final concentration of 0.5, 0.25, and 0.05% (22 mM, 11 mM, and 2 mM) BM3103. Tobramycin (600 μg/mL) served as the positive control. Vehicle and BM3103 formulations contained matching final concentration of 35% v/v alcohol.

Transcutol Formulations

BM3103 was dissolved into Transcutol (diethylene glycol monoethyl ether) at 2.5% w/v and vortexed until dissolved. This concentration was then serial diluted to achieve the remaining concentrations tested. Before plating, 100 μL of the final inoculum ($10^8$ CFU/mL) was mixed with 20 μL TSB broth and 80 μL of BM3103 doses or vehicle. Tobramycin, 600 μg/mL, served as the positive control. The final plating concentrations for BM3103 were 1, 0.5, 0.25, and 0.1% w/v (44 mM, 22 mM, 11 mM, 4 mM) BM3103. Vehicle and BM3103 formulations contained matching final concentration of 40% v/v Transcutol.

Plating and Counting Colonies

The above listed formulations combined with the MRSA inoculum were plated onto TSB agar plates. The plates were grown at 37° C. for 24 h, imaged, and the bacteria colonies were counted. The experiment was done in triplicate at each concentration level described above. Colony counts for each treatment were tabulated and the Log of the colony forming units/mL (Log CFU/mL) were determined. The mean and the standard error of the mean were calculated for each treatment.

Figure 9:
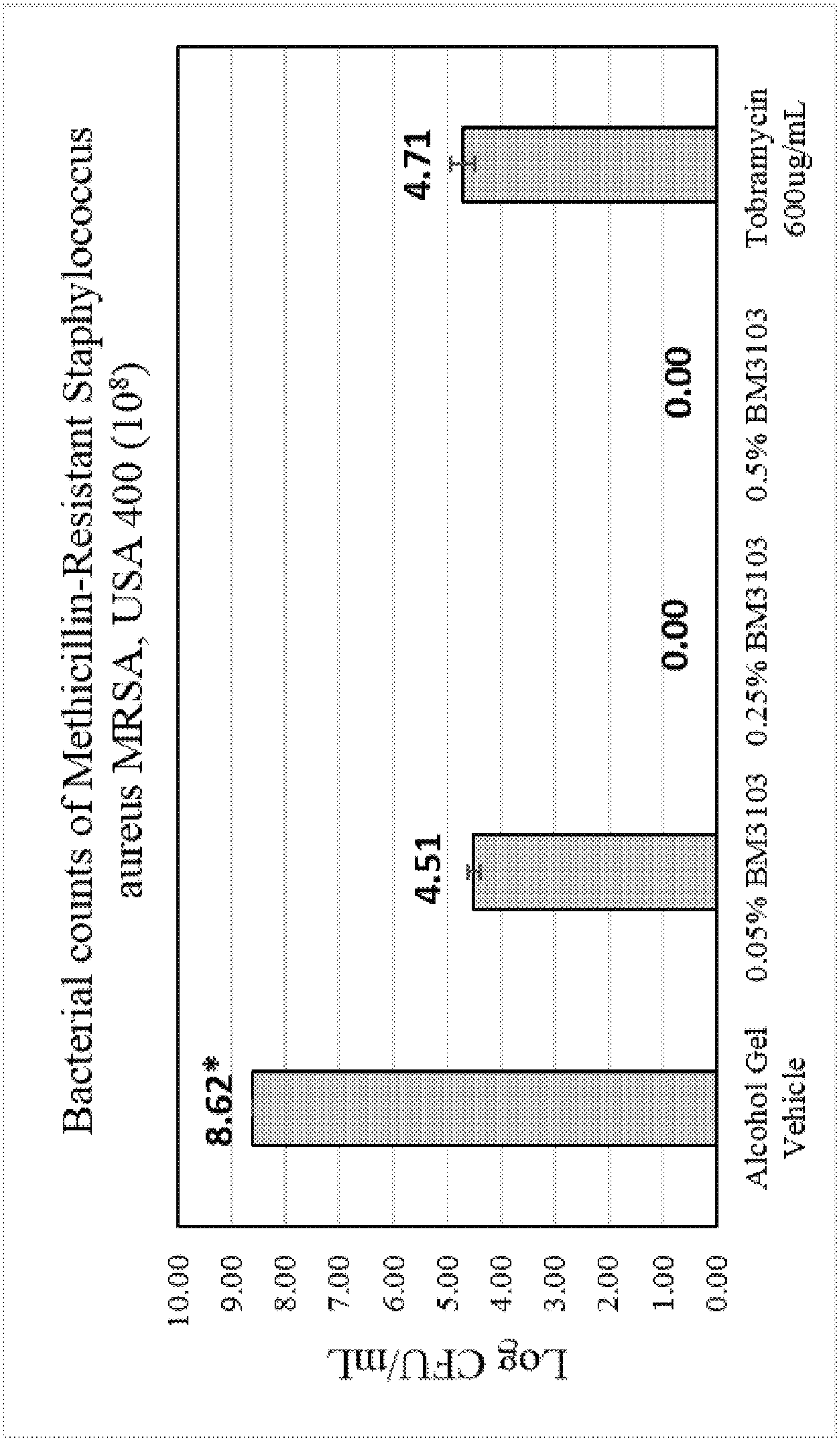
FIG. 9 is a graph showing bacterial counts of MRSA USA 400 after 24 h plate assay of BM3103 in an alcohol gel formulation.
Figure 10:
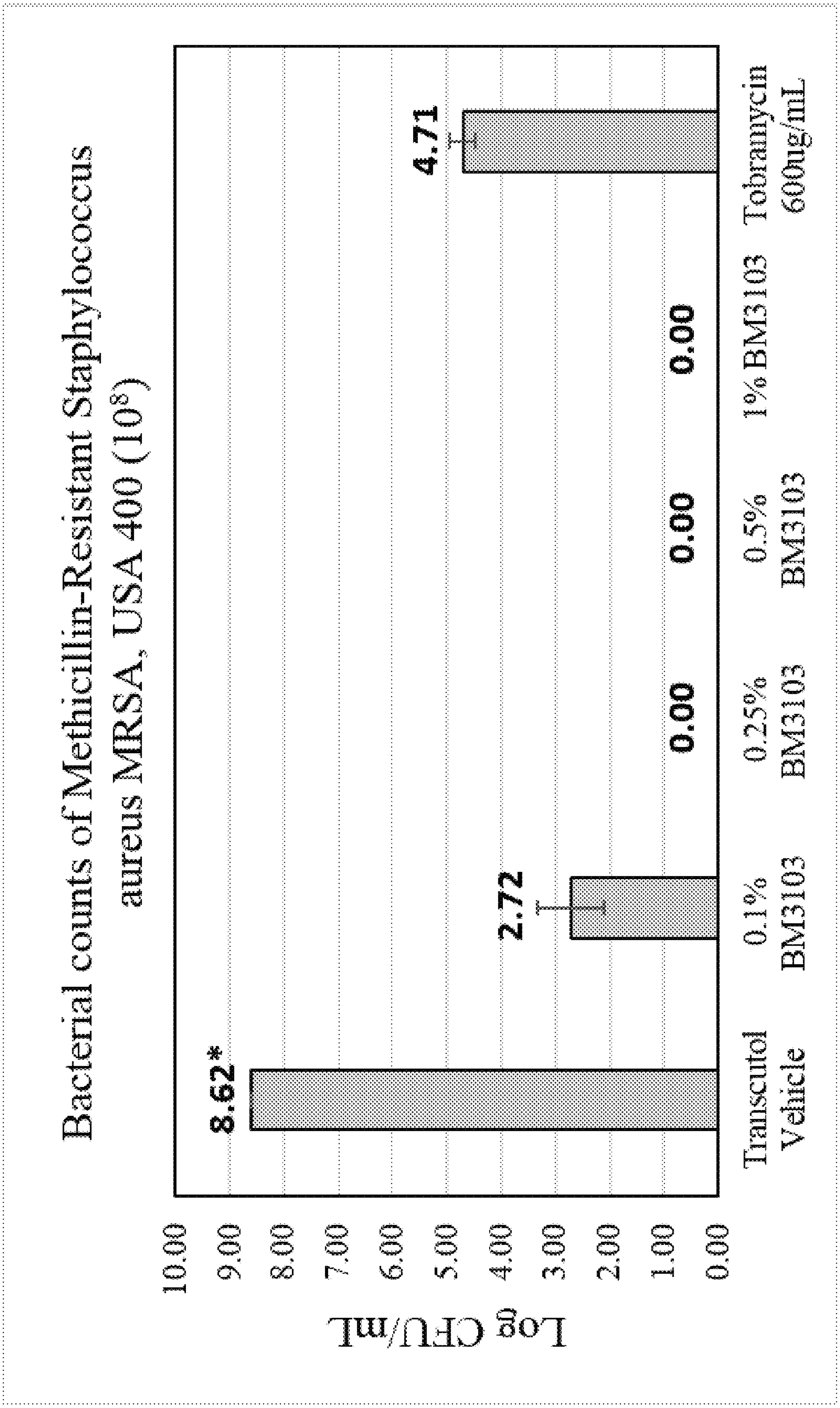
FIG. 10 is a graph showing bacterial counts of MRSA USA 400 after 24 h plate assay of BM3103 in a Transcutol formulation.

As seen in FIG. 9, 0.5 and 0.25% BM3103 in the alcohol gel formulation resulted in no bacterial count for MRSA USA 400. The positive control, Tobramycin, and the lowest dose of BM3103 (0.05% w/v, 2 mM), reduced the counts significantly by 4-fold when compared to the vehicle control. For the Transcutol formulation, FIG. 10 shows more than a 5-fold reduction for 0.1% BM3103. There was no bacterial count for MRSA USA 400 for the remaining concentrations of BM3103 tested in the Transcutol formulation.

Example 14: *Acinetobacter baumannii* Inoculum

Proliferating cultures of *Acinetobacter baumannii* were used in a colony forming assay. Frozen stock cultures of *Acinetobacter baumannii* were thawed and grown overnight in tryptic soy broth (TSB) with shaking at 37° C. The overnight culture (0.5-1.0 mL) was added to 100 mL TSB and grown at 37° C. with shaking and monitored for an optical density of 0.20-0.38 to obtain a final inoculum suspension of approximately $10^8$ CFU/mL.

Transcutol Formulations

BM3103 was dissolved into Transcutol (diethylene glycol monoethyl ether) at 2.5% w/v and vortexed until dissolved. This concentration was then serial diluted to achieve the remaining concentrations tested. Before plating, 100 μL of the final inoculum ($10^8$ CFU/mL) was mixed with 20 μL TSB broth and 80 μL of BM3103 doses or vehicle. Tobramycin, 600 μg/mL, served as the positive control. The final plating concentrations for BM3103 were 1, 0.5, 0.25, and 0.1% w/v (44 mM, 22 mM, 11 mM, 4 mM) BM3103. Vehicle and BM3103 formulations contained matching final concentration of 40% v/v Transcutol.

Plating and Counting Colonies

The Transcutol formulations combined with the inoculum were plated onto TSB agar plates. The plates were grown at 37° C. for 24 h, imaged, and the bacteria colonies were counted. The experiment was done four times at each concentration level described above. Colony counts for each treatment were tabulated and the Log of the colony forming units/mL (Log CFU/mL) were determined. The mean and the standard error of the mean were calculated for each treatment.

Figure 11:
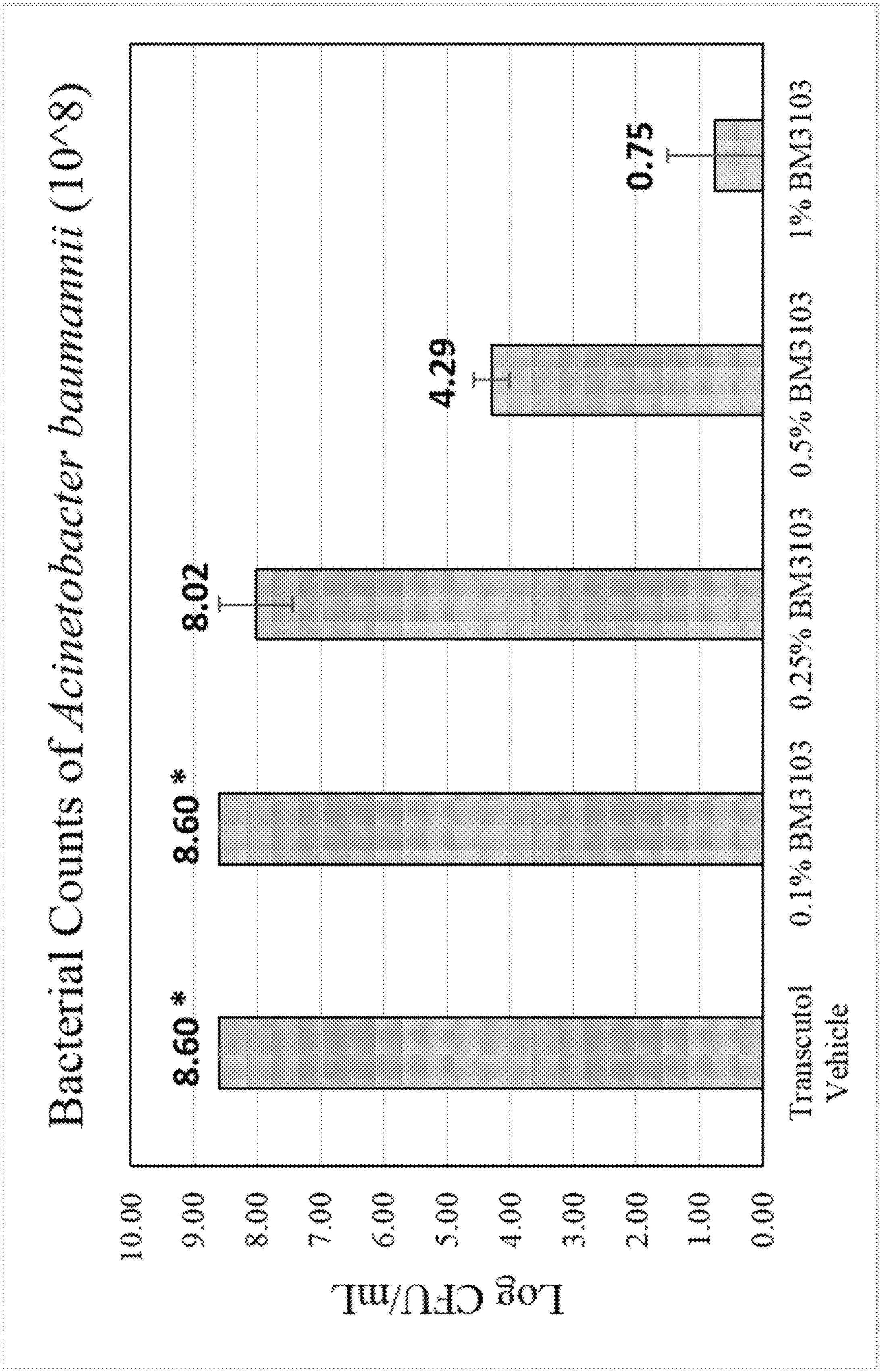
FIG. 11 is a graph bacterial counts of *A. baumannii* after 24 h plate assay of BM3103 in a Transcutol formulation.

As shown in FIG. 11, the lowest concentration tested of BM3103 at 0.1% resulted in no reduction of *Acinetobacter baumannii*. A slight reduction in bacterial counts was seen at 0.25% BM3103. BM3103 at 0.5% resulted in a 4-fold reduction of bacterial counts, and 1% BM3103 resulted in almost a complete reduction of *Acinetobacter baumannii* (with only one colony present on one of the plates tested).

Example 15: Biofilm Formation Assays

Proliferating cultures of Methicillin Resistant *Staphylococcus aureus* (MRSA, USA 400) were used in a colony forming assay. Frozen stock cultures of MRSA USA 400 were thawed and grown overnight in tryptic soy broth (TSB) with shaking at 37° C. The overnight culture (0.5-1.0 mL) was added to 100 mL TSB and grown at 37° C. with shaking and monitored for an optical density of 0.55-0.60 in order to obtain a final inoculum suspension of approximately $10^8$ CFU/mL.

Prevention of Biofilm Formation

Figures 12A, 12B, 12C, 12D:
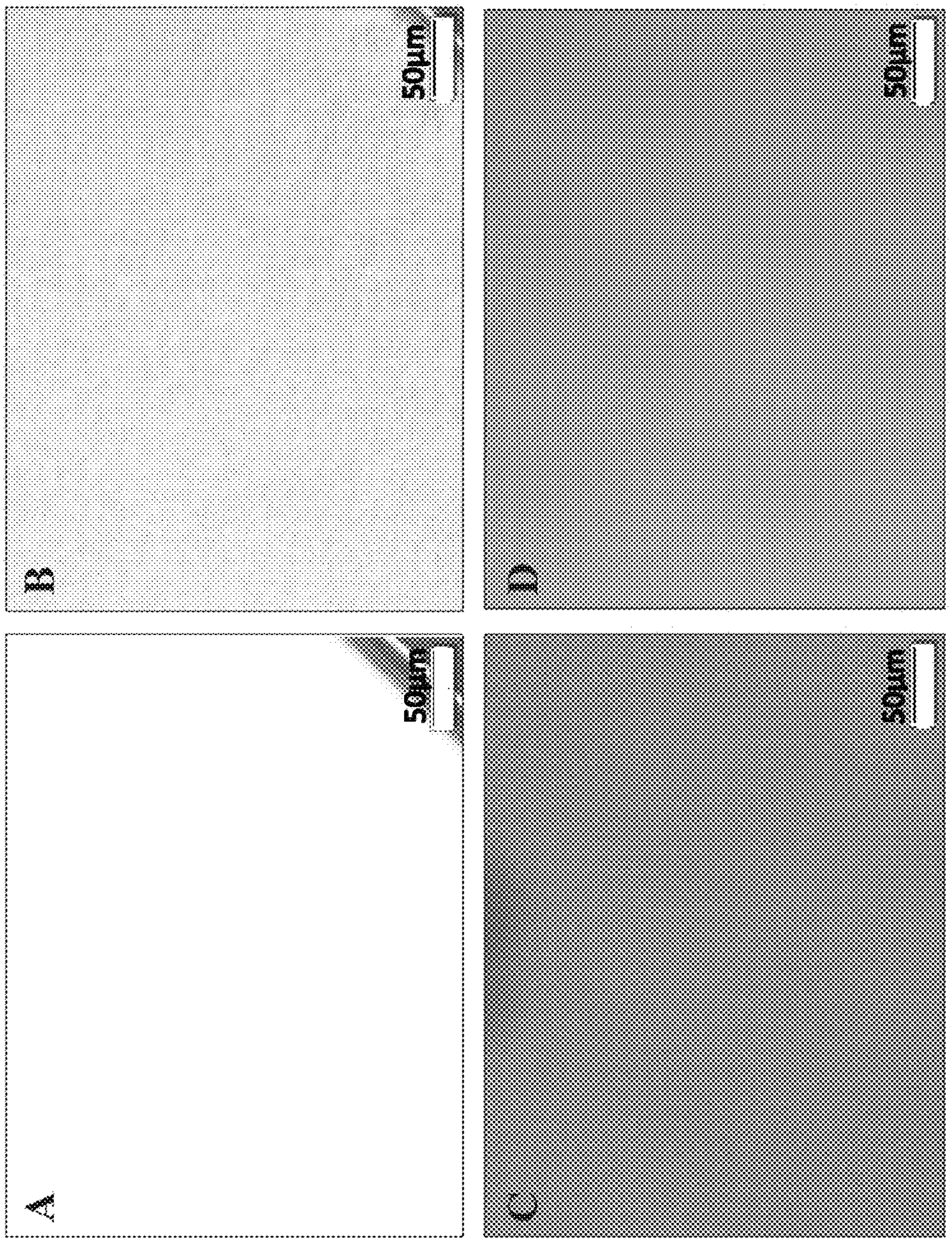
FIGS. 12A-12D are images showing the results of a biofilm inhibition assay of MRSA USA 400.

For the biofilm inhibition assay, 100 μL of MRSA USA 400 inoculum ($10^8$ CFU/mL) was plated with 100 μL of each BM3103 drug concentration in a 96 well plate. A 0.1 M stock of BM3103 was dissolved in ethanol and serially diluted in TSB across a 96 well plate to obtain final concentrations of 1 mM to 0.002 mM. The drug treated inoculum grew overnight at 37° C. without shaking. Images were taken of each concentration and representative images are shown in FIGS. 12A-12D. At a concentration of 0.625 mM, BM3103 inhibits biofilm formation of MRSA USA 400 completely (FIG. 12A). Mild biofilm formation is present at 0.008 mM BM3103 (FIG. 12B). At concentrations of about 0.002 mM, BM3103 has no effect on biofilm formation of MRSA USA 400, and is comparable to control wells that were not treated with BM3103 (FIGS. 12C-12D). Overall, BM3103 completely inhibits biofilm formation at concentrations above 0.0625 mM and reduces biofilm formation at concentrations between 0.03125 mM and 0.008 mM.

Bacterial Cell Death

Figure 13:
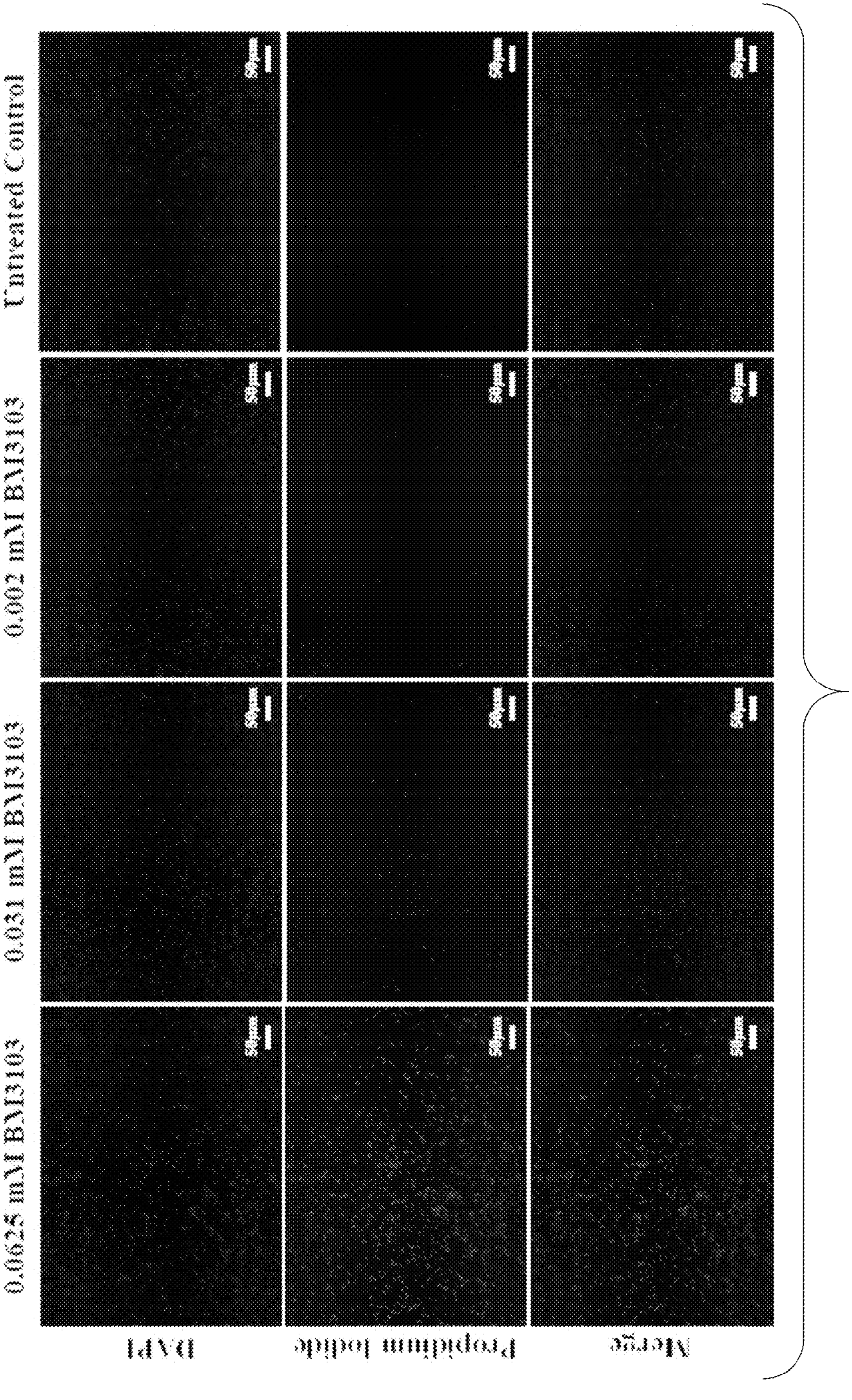
FIG. 13 is a series of images showing BM3103 treatment of MRSA USA 400 induces cell death as shown by positive PI staining.
Figures 14A, 14B, 14C, 14D:
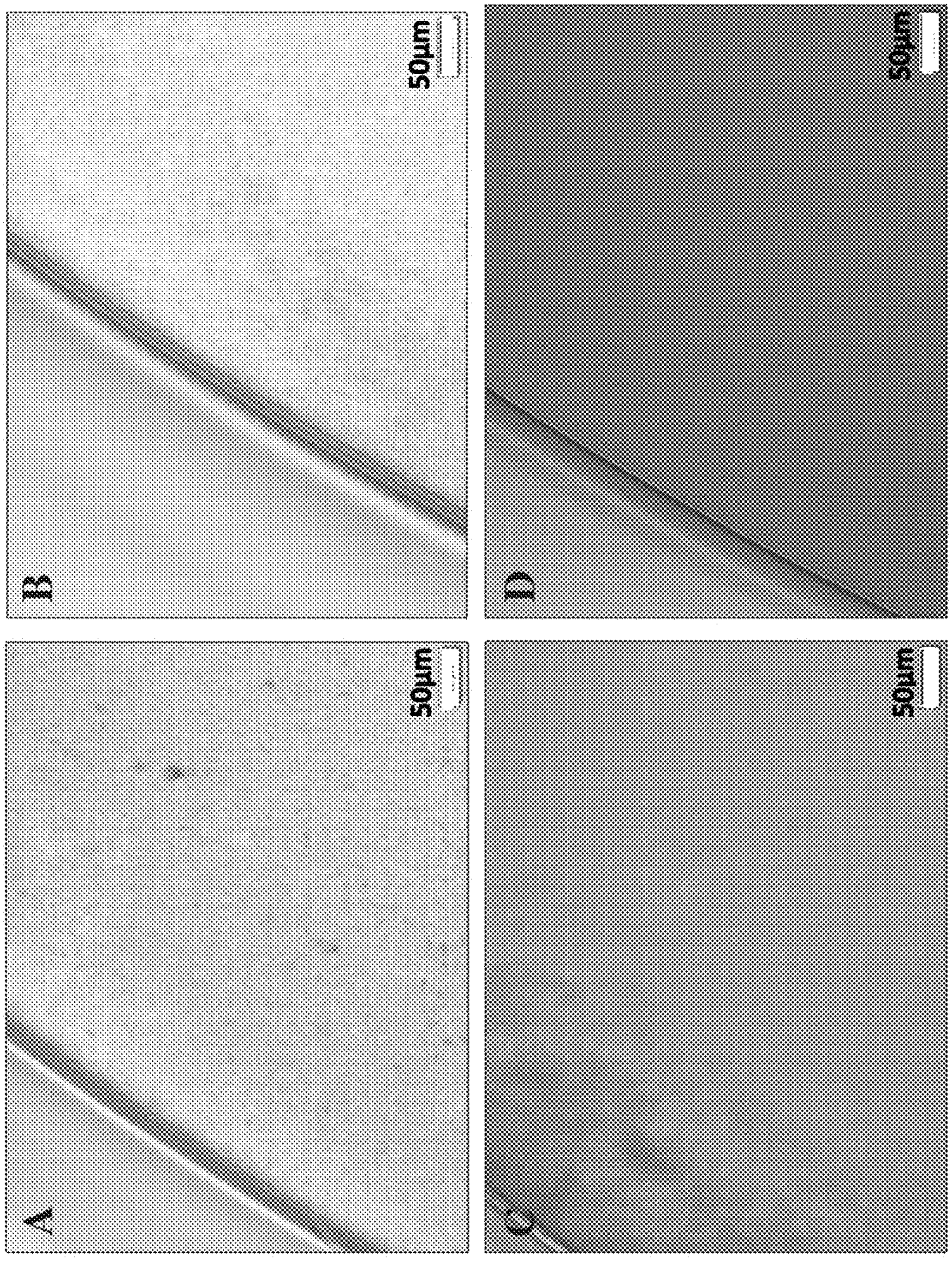
FIGS. 14A-14D are images showing treatment of an established MRSA USA 400 biofilm with BM3103 for 24 h.

In order to confirm that treatment with BM3103 induced MRSA USA 400 bacterial cell death, both untreated cells and cells treated with BM3103 were stained with a combination of DAPI (nuclear stain) and Propidium iodide (PI, Live dead stain). In a healthy cell, PI is not able to cross the cell membrane and produces no fluorescent signal. If the cell is dead or has a compromised cell membrane it will bind DNA and fluoresces between 535 nm excitation and 617 nm emission. MRSA USA 400 were plated in a well plate at $10^8$ CFU/mL in combination with BM3103 treatment or no treatment. Plates were placed at 37° C. for 24 h. Bacteria cells were co-stained with DAPI and PI at 50 μg/mL and 500 μg/mL, respectively, for 15 min at room temperature. Wells were washed with warmed phosphate buffered saline (PBS) and maintained in PBS throughout the imaging acquisition process. Images were captured using the same exposure limits for each filter. In this experiment untreated cells showed strong DAPI staining with only light and sparse staining of PI, indicating bacteria within the biofilm were alive (FIG. 13). After 24 h treatment with BM3103, there was a dose dependent increase in PI staining from 0.002 mM to 0.0625 mM, indicating the majority of the bacteria were either dead or dying (FIG. 13). Concentrations above 0.0625 mM gave a similar result.

Treatment of an Existing Biofilm

For the treatment of MRSA USA 400 biofilms, the same 96 well plate assay procedure was used as described in the biofilm inhibition section above. However, the MRSA USA 400 inoculum ($10^8$ CFU/mL) grew overnight at 37° C. in the absence of BM3103 and without shaking. After 24 h of biofilm formation, BM3103 was serially diluted across a 96 well plate from of 1 mM to 0.002 mM. The plate was incubated again overnight at 37° C. without shaking. After a total of 48 h, images of each concentration were taken and representative images are shown in FIGS. 14A-14D. At concentrations of 0.125 mM (FIG. 14A), 0.0625 mM (FIG. 14B) or above, BM3103 reduced the biofilm of MRSA USA 400 significantly. At 0.008 mM (FIG. 14C) there was still a slight reduction in the biofilm but at concentrations below 0.002 mM or in untreated controls (FIG. 14D), no reduction in the biofilm was observed.

Cell Death in an Existing Biofilm

For the treatment of MRSA USA 400 biofilms, the same 96 well plate assay procedure was used as described in the biofilm inhibition section above. However, the MRSA USA 400 inoculum ($10^8$ CFU/mL) grew overnight at 37° C. in the absence of BM3103 and without shaking. After 24 h of biofilm formation, BM3103 was serially diluted across a 96 well plate from of 1 mM to 0.002 mM. The plate was incubated again overnight at 37° C. without shaking.

Figure 15:
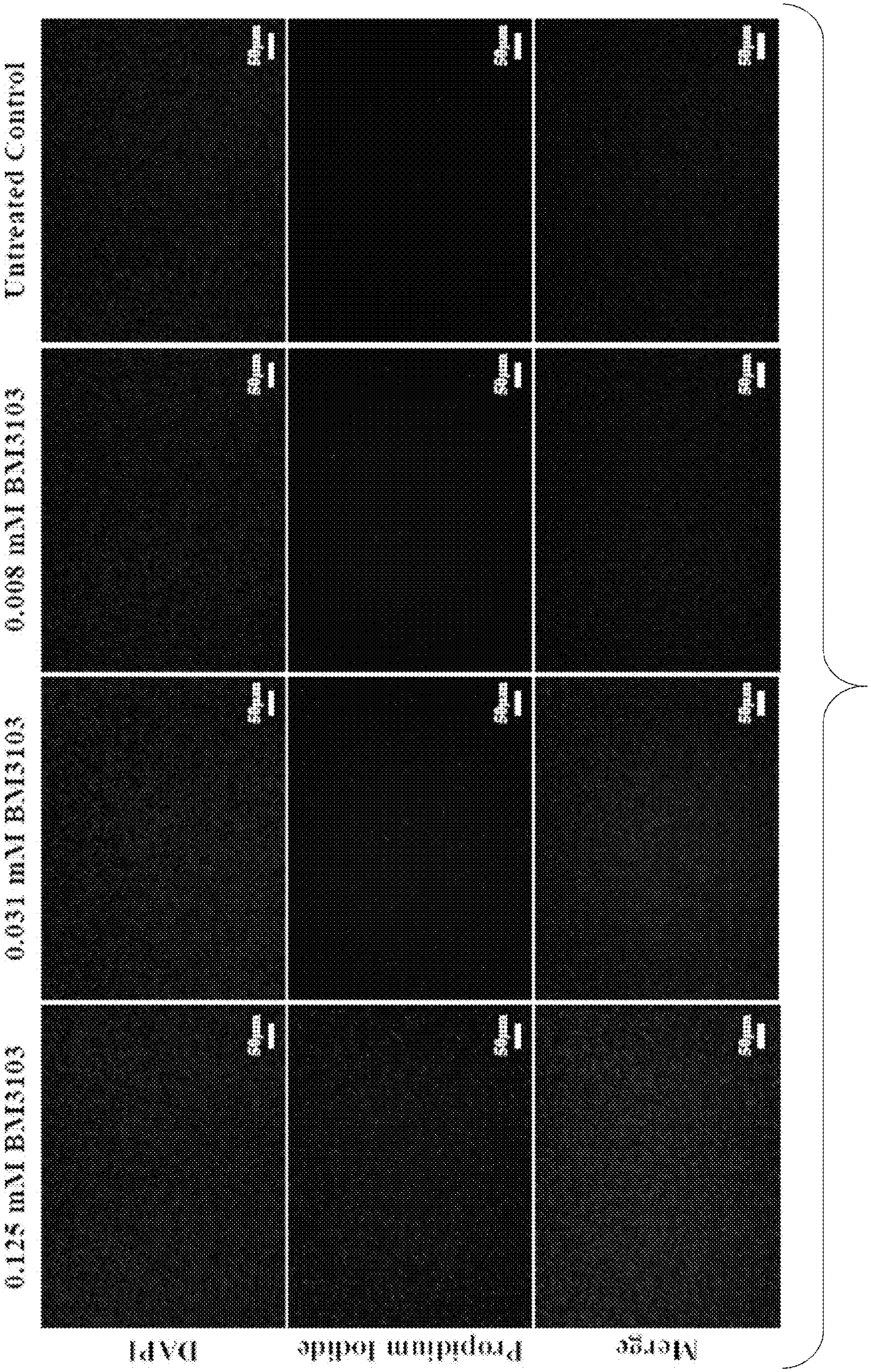
FIG. 15 is a series of images showing BM3101 treatment of MRSA USA 400 induces cell death in an existing biofilm as shown by positive PI staining.

In order to confirm that treatment with BM3103 induced MRSA USA 400 bacterial cell death in the existing biofilm, both untreated cells and cells treated with BM3103 were stained with a combination of DAPI (nuclear stain) and Propidium iodide (PI, Live dead stain) as described in Example 15. MRSA USA 400 were plated in a well plate at $10^8$ CFU/mL in combination with BM3103 treatment or no treatment. Plates were placed at 37° C. for 24 h. Bacteria cells were co-stained with DAPI and PI at 50 μg/mL and 500 μg/mL, respectively, for 15 min at room temperature. Wells were washed with warmed phosphate buffered saline (PBS) and maintained in PBS throughout the imaging acquisition process. Images were captured using the same exposure limits for each filter. In this experiment, untreated cells showed strong DAPI staining with only light and sparse staining of PI, indicating bacteria within the biofilm were alive (FIG. 15). After 24 h treatment with BM3103, there was a dose dependent increase in PI staining from 0.008 mM to 0.125 mM, indicating the majority of the bacteria were either dead or dying within the biofilm (FIG. 15). Concentrations above 0.125 mM gave a similar result.

The foregoing description of the various aspects and embodiments of the present invention has been presented for purposes of illustration and description. It is not intended to be exhaustive of all embodiments or to limit the invention to the specific aspects disclosed. Obvious modifications or variations are possible in light of the above teachings and such modifications and variations may well fall within the scope of the invention as determined by the appended claims when interpreted in accordance with the breadth to which they are fairly, legally and equitably entitled.

What is claimed is:

1. An antimicrobial formulation comprising an antimicrobially effective amount of a compound having the structure (I):

(I)

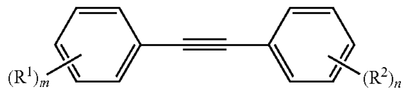

or a salt thereof, wherein:

each $R^1$ is independently $C_1$-$C_6$ $(halo)_p$alkyl, $C_1$-$C_6$ alkyl-RH, OH, $OC_1$-$C_6$ alkyl, or SH;

each $R^2$ is independently $C_1$-$C_6$ $(halo)_p$alkyl, $C_1$-$C_6$ alkyl-RH, OH, $OC_1$-$C_6$ alkyl, or SH;

each R is independently O or S;

m is 1, 2, or 3;

n is 1, 2, or 3; and each p is independently 1, 2, or 3;

with the provisos that:

(1) the compound having the structure (I) is mixed into an alcohol gel; and (2) the compound having the structure (I) is not:

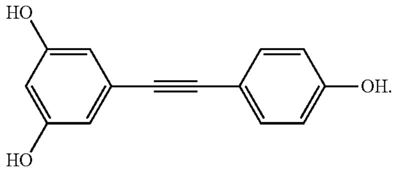 [SMILES: Oc1ccc(C#Cc2cc(O)cc(O)c2)cc1]

2. The antimicrobial formulation of claim 1, wherein the antimicrobial formulation is phenol free.

3. The antimicrobial formulation of claim 1, wherein the antimicrobial formulation comprises the compound having the structure (I), or a salt thereof, mixed into a 35% v/v alcohol gel.

4. The antimicrobial formulation of claim 1, wherein the antimicrobial formulation comprises a concentration of the compound having the structure (I), or a salt thereof, in an amount ranging from 2 mM to 44 mM.

5. The antimicrobial formulation of claim 1, wherein the antimicrobial formulation comprises a concentration of the compound having the structure (I), or a salt thereof, in an amount ranging from 0.008 mM to 1 mM.

6. The antimicrobial formulation of claim 1, wherein the antimicrobial formulation comprises a concentration of the compound having the structure (I), or a salt thereof, in an amount ranging from 0.01% w/w to 30% w/w.

7. The antimicrobial formulation of claim 1, wherein the antimicrobial formulation comprises a concentration of the compound having the structure (I) in an amount ranging from 0.25% w/v to 1% w/v.

8. The antimicrobial formulation of claim 1, wherein the compound having the structure (I) is:

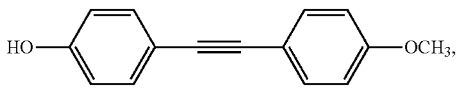 [SMILES: COc1ccc(C#Cc2ccc(O)cc2)cc1]

or a salt thereof.

9. The antimicrobial formulation of claim 8, wherein the antimicrobial formulation comprises the compound having the structure (I), or a salt thereof, mixed into a 70% v/v alcohol gel.

10. The antimicrobial formulation of claim 8, wherein the antimicrobial formulation comprises a concentration of the compound having the structure (I), or a salt thereof, in an amount ranging from 2 mM to 44 mM.

11. The antimicrobial formulation of claim 8, wherein the antimicrobial formulation comprises a concentration of the compound having the structure (I), or a salt thereof, in an amount ranging from 0.008 mM to 1 mM.

12. The antimicrobial formulation of claim 8, wherein the antimicrobial formulation comprises the compound having the structure (I), or a salt thereof, at a concentration of 0.0625 mM.

13. The antimicrobial formulation of claim 8, wherein the antimicrobial formulation comprises the compound having the structure (I), or a salt thereof, at a concentration of 0.008 mM.

14. The antimicrobial formulation of claim 8, wherein the antimicrobial formulation comprises a concentration of the compound having the structure (I), or a salt thereof, in an amount ranging from 0.01% w/w to 30% w/w.

15. The antimicrobial formulation of claim 1, wherein the antimicrobial formulation further comprises an antibiotic.

16. The antimicrobial formulation of claim 1, wherein the antimicrobial formulation further comprises a solvent.

17. The antimicrobial formulation of claim 1, wherein the antimicrobial formulation further comprises a detergent, an emollient, a soap, or a surfactant.

18. The antimicrobial formulation of claim 1, wherein the antimicrobial formulation further comprises PEG-400 and hydroxypropyl-β-cyclodextrin in water.

19. The antimicrobial formulation of claim 18, wherein:

(a) the compound having the structure (I) is:

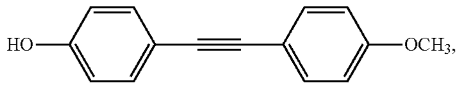

or a salt thereof; and (b) the compound, or salt thereof, is mixed into a 70% v/v alcohol gel.

20. The antimicrobial formulation of claim 1, wherein the antimicrobial formulation further comprises:

(a) 30% v/v PEG-400;

(b) hydroxypropyl-β-cyclodextrin in water in an amount ranging from 0% to 28%;

(c) the compound having the structure (I):

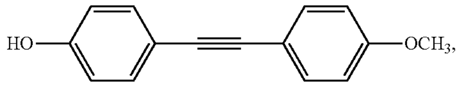 [SMILES: COc1ccc(C#Cc2ccc(O)cc2)cc1]

or a salt thereof; and (d) the compound, or salt thereof, mixed into a 70% v/v alcohol gel.

* * * * *